United States Patent [19]
Yamada et al.

[11] Patent Number: 5,211,657
[45] Date of Patent: May 18, 1993

[54] LAMININ A CHAIN DEDUCED AMINO ACID SEQUENCE, EXPRESSION VECTORS AND ACTIVE SYNTHETIC PEPTIDES

[75] Inventors: Yoshihiko Yamada, Silver Spring, Md.; Makoto Sasaki, Beppu, Japan; Hynda K. Kleinman; George R. Martin, both of Bethesda, Md.

[73] Assignee: The United States Government as represented by the Secretary of the Department of Health and Human Services, Washington, D.C.

[21] Appl. No.: 267,564

[22] Filed: Nov. 7, 1988

[51] Int. Cl.$^5$ .......................... A61F 2/06; A61F 2/02
[52] U.S. Cl. .......................................... 623/1; 623/11; 623/66; 623/12; 514/13; 514/14; 514/15; 530/326; 530/327
[58] Field of Search ............................... 514/2, 13–15; 530/322, 326, 327, 328, 331; 623/1, 11, 12, 66

[56] References Cited

U.S. PATENT DOCUMENTS

| | | |
|---|---|---|
| 4,340,581 | 7/1982 | Timpl . |
| 4,497,799 | 2/1985 | Yoshizumi et al. . |
| 4,565,789 | 1/1986 | Liotta et al. . |
| 4,609,629 | 9/1986 | Timpl . |
| 4,614,517 | 9/1986 | Ruoslahti et al. . |
| 4,642,293 | 2/1987 | Chung . |
| 4,714,643 | 12/1987 | Shoyab et al. . |
| 4,870,160 | 9/1989 | Charonis et al. ............ 530/326 |
| 4,876,332 | 10/1989 | Tsilibary et al. ............ 530/326 |

OTHER PUBLICATIONS

Graf et al, "A Pentapeptide from the Laminin B1 Chain Mediates Cell Adhesion and Binds the 67 000 Laminin Receptor", *Biochemistry*, Nov. 3, 1987, pp. 6896–6900.

Iwamoto et al, "Synthetic Pentapeptide From the B1 Chain of Laminin Promotes a B16F10 Melanoma Cell Migration", *Journal of Cellular Physiology*, vol. 134, pp. 287–291 (1988).

Terranova, "Regulation of Cell Attachment and Cell Number by Fibronectin and Laminin", *Journal of Cellular Physiology* 127:473–479 (1986).

Barsky, Laminin Molecular Domains which Alter Metastasis in a Murine Model *J. Clin. Invest.*, vol. 74, Sep. 1984, pp. 843–848.

Graf, "Identification of an Amino Acid Sequence in Laminin Mediating Cell Attachment, Chemotaxis, and Receptor Binding", *Cell*, vol. 48, pp. 989–996.

Sasaki, Sequence of the cDNA Encoding the Laminin B1 Chain Reveals a Multi-Domain Protein Containing Cystein-Rich Repeat, *Proc. Natl. Acad. Sci.*, vol. 84, pp. 935–939.

Iwamoto et al, "YIGSR, a Synthetic Laminin Pentapeptide, Inhibits Experimental Metastasis Formation", *Science*, vol. 238, pp. 1132–1134.

*Primary Examiner*—Alan W. Cannon
*Attorney, Agent, or Firm*—Birch, Stewart, Kolasch & Birch

[57] ABSTRACT

The present invention relates to peptides and derivatives thereof having laminin-like activity. The invention further relates to pharmaceutical compositions containing these peptides, to antibodies effective against these peptides, and to vectors containing a DNA sequence of cDNA coding for the A chain of laminin. The peptides of the invention may be used to treat diseases such as cancer.

17 Claims, 42 Drawing Sheets

FIG.4-1

```
AGCACGGGCGAGACCTTCCCAGGAGCCAGGAGCGGGCGACAACATGCGGGGCACGGGAGCGCCTCCTGGTGCTCCTGGCCTCGGTGCTC
                                      M  R  G  S  G  T  G  A  A  L  L  V  L  L  A  S  V  L
                                                     -20                              -10
TGGGTCACCGTGCGGAGC                                                      120
 W  V  T  V  R  S
         -1
CAGCAGAGAGGCTTGTTCCCTGCCATTCTCAACCTGGCCACCAATGCCCACATCAGCGCCAATGTACTCTGTGGAGAGAAGGGCCCTGAGATGTTCTGCAAA
 Q  Q  R  G  L  F  P  A  I  L  N  L  A  T  N  A  H  I  S  A  N  A  T  G  E  K  G  P  E  M  F  C  K
                                                              N  A  T
CTCGTGGAGCACGTGCCG                                                      240
 L  V  E  H  V  P
+1                                              10
GGCCGGCCCGTGTTCGACACGCCCAATGCCCAGGTCTGTGACGGTAACAGTACGAATCCTAGAGAGCGCCATCCGATATCACACGCAATGCCACCAACAAC
 G  R  P  V  R  H  A  Q  R  V  C  D  G  N  S  T  N  P  R  E  R  H  P  I  S  H  A  I  D  G  T  N  N
                            40           D  G  N  S  T
TGGTGCCAGAGCCCCAGT                                                      360
 W  W  Q  S  P  S
                                                     50                              70
ATTCAGAATGGGAGAGAGTATCACTGGGTCACTGTCACCCTGGACTTACGGCAGGTCTTTCAAGTTGCATACATCATCATTAAAGCTGCCAATGCCCCTCGG
 I  Q  N  G  R  E  Y  H  W  V  T  V  T  L  D  L  R  Q  V  F  Q  V  A  Y  I  I  I  K  A  A  N  A  P  R
                         80
CCTGGAAACTGGATTTTG                                                      480
 P  G  N  W  I  L
                                                     90                              110
GAGCGCTCCGTGGATGGCGTCAAGTTCAAACCCTGGCAGTACTATGCCGTCAGCGATACAGAGTGTTTGACCCGCTACAAAATAACTCCACGGGGGGACCT
 E  R  S  V  D  G  V  K  F  K  P  W  Q  Y  Y  A  V  S  D  T  E  C  L  T  R  Y  K  I  T  P  R  R  G  P
                        120
CCCACTTACAGAGCAGAC                                                      600
 P  T  Y  R  A  D
                                                     130                             150
AACGAAGTCATCTGCACCTCGTATTATTCAAAGCTGGTGCCACTTGAACATGGAGAGATTCACACATCACTCATCAATGGCAGACCCAGCGCTGACGACCCC
 N  E  V  I  C  T  S  Y  Y  S  K  L  V  P  L  E  H  G  E  I  H  T  S  L  I  N  G  R  P  S  A  D  D  P
                       160
TCACCCCAGTTGCTGGAA                                                      720
 S  P  Q  L  L  E
```

FIG.4-2

```
                              170                        180                       190
TTCACCTCAGCACGGTACATTGCGCCTTCGTCTTCAGGCCATCAGAGACACTCAACGCAGAGACCTCATGACCCTTAGCCATCGGGACCTCAGAGACCTTGACCCC
 F  T  S  A  R  Y  I  R  L  R  L  Q  R  I  R  T  L  N  A  D  L  M  T  L  S  H  R  D  L  R  D  L  D  P
ATTGTCACAAGAGACGTTAT      840
 I  V  T  R  R  Y
                              210                        220                       230
TACTATTCGATAAAAGACATTCCGTTGGAGGCCATGTGCATTTGCATTGTGC©YGGHASS©PWDEEAKQLQ©Q
 Y  Y  S  I  K  D  I  S  V  G  G  M ©  I ©  Y  G  H  A  S  S ©  P  W  D  E  E  A  K  Q  L  Q ©  Q
TGTGAACACAATACGTGT      960
 ©  E  H  N  T ©
                              250                        260                       270
GGGGAGAGCTGGCGACAGTTGCTG©CCTGGCTACCATCAGCAGCCCTGAGGCCCCGAACGACTGTGAGGAATGCAACTGTCACAAC
 G  E  S ©  D  R ©  P  G  Y  H  Q  Q  P  W  R  P  G  T  I  S  S  G  N  E ©  E ©  N ©  H  N
AAAGCCAAAGATTGTTAC     1080
 K  A  K  D ©  Y
                              290                        300                       310
TATGACACAGTCGTTGCAAAGGAGAGAAGGAGAGCCTGAACACTGCCGGGCAGTACAGTGGCGGAGGGGTTTGTCAACTGTCAAGAATACCACAGGGATC
 Y  D  S  S  V  A  K  E  R  R  S  L  N  T  A  G  Q  Y  S  G  G  G  V ©  V  N ©  S  Q  N  T  T  G  I
AACTGTGAAACCTGTATC     1200
 N ©  E  T ©  I
                              330                        340                       350
GACCAGTATTACAGACCTCCACAAGGTATCTCCTTATGATGACCACCCTGCCTCCCTGTAACTGTGAC©DPVGSLSSV©IK
 D  Q  Y  Y  R  P  H  K  V  S  P  Y  D  D  H  P ©  R  P ©  N ©  D  P  V  G  S  L  S  S  V ©  I  K
GATGACCGCCATGCCGAT     1320
 D  D  R  H  A  D
                              370                        380                       390
TTAGCCAATGAAGTGGCCAGTCAGTGTCCATGTAGGAAAGGTTATGCTGGAGATAAATGTGACCGCTGCCAGTTGGCTACCGGGGTTTCCAAATTGC
 L  A  N  G  K  W  P  G  Q ©  P ©  R  K  G  Y  A  G  D  K ©  D  R ©  Q  F  G  Y  R  G  F  P  N ©
ATCCCCCTGTGACTGCAGG   1440
 I  P ©  D ©  R
```

FIG.4-3

```
ACTGTCGGCAGCCTGAATGAGGATCCATGCAATGAGCCGTGTCTTTGTAAGAAAAATGTTGAGGGTAAGAACTGTGATCGCTGCAAGCCAGGATTCTACAAC
 T  V  G  S  L  N  E  D  P ©I  E  P © L © K  K  K  N  V  E  G  K  N ©D  R ©K  P  P  G  F  Y  N
                 410              420              430
                                 1560
TTGAAGGAACGAAACCCC
 L  K  E  R  N  P

GAGGGCTGCTCCGAGTGCTTCTGTGGTGTCTCTGGTGTCTGTGTCTGTCTGGTGTCTTGACAGCCTCACGTGGTCCATTAGTCAGGTTGACCAATATGTCAGGTGGCTGCTGTCACT
 E  G © S  E © F © F  F  G  V  S  G  V © D  S  L  T  W  S  I  S  Q  V  T  N  M  S  G  W  L  V  T
                 450              460              470
                                 1680                                                    ==========
GACTTGATGAGCACAAAT
 D  L  M  S  T  N
            480

AAGATCCGGTCCCAGCAAGATGTCCTGGGTGTGGGCCACCGTCAGATCAGCAGGCTCATGCAGCGGCTCATGCAGCGGTCATGCAGCGGCTGACTTCCACTTACTACTGGGCAGCT
 K  I  R  S  Q  Q  D  V  L  G  G  H  R  Q  I  S  I  N  N  T  A  V  M  Q  R  L  T  S  T  Y  Y  W  A  A
        520              490              500              510
                                                           =====                           ====
CCTGAGGCCTACCTCGGA
 P  E  A  Y  L  G
                  1800

AACAAGCTGACAGCATTTGGCGGTTTCCTGAAATACACTGTCTCTTACGACATTCCAGTGGAGACGGTGACCTCATGTCTCATGCTGACATCATC
 N  K  L  T  A  F  G  G  F  L  K  Y  T  V  S  Y  D  I  P  V  E  T  V  D  S  D  L  M  S  H  A  D  I  I
                 530              540              550
                                                =====
ATCAAGGGGAATGGGCTC
 I  K  G  N  G  L
            560                  1920

ACCATAAGCACAAGAGCTGAGGGCCTGTCCTTGCAACCCTATGAGGAATACTTCAACGTGGTTAGACTTGTGCCTGAGAACTTCCGGGACTTTAATACCAGA
 T  I  S  T  R  A  E  G  L  S  L  Q  P  Y  E  E  Y  F  N  V  V  R  L  V  P  E  N  F  R  D  F  N  T  R
                 570              580              590

AGGGAGATTGACCGTGAC
 R  E  I  D  R  D
            600                  2040

CAGCTGATGACTGTCCTGGCCAATGTGACACATCTCTTGATCAGAGCCAATTATAATTCTGCTAAAATGGCCCTCTATAGGCTGGATTCTGTCTCTCTGGAC
 Q  L  M  T  V  L  A  N  V  T  H  L  L  I  R  A  N  Y  N  S  A  K  M  A  L  Y  R  L  D  S  V  S  L  D
                 610              620              630
                       ====
ATAGCAAGCCCTAATGCT
 I  A  S  P  N  A
            640                  2160
```

FIG.4-4

```
ATAGACTTGGCAGTGGCTGCTGATGTGGAACACTGTGAATGTCCCCAAGGCTACACGGGACCTCCTGTGAGGCCTGCCTGGCTATTATCGAGTGGAC   670
 I  D  L  A  V  A  A  D  V  E  H ©E ©P  Q  G  Y  T  G  T  S ©E  A ©L  P  G  Y  Y  R  V  D

GGGATACTCTTTGGAGGA   2280
 G  I  L  F  G  G
                                                                                                   710
ATCTGTCAGCCCTGCCAGTGCCACGGGCCATCGAGTGTCCAGTGTCATTCATGAATTTGCTCTGTGTACACACAACACCGGGATCACTGTGAGCCAG
 I ©Q  P ©E ©H  G  H  A  S  E ©D  I  H  G  I ©S  V ©T  H  N  T  T  G  D  H ©E  Q

TGCCTGCCTGGCTTCTAT   2400
©L  P  G  F  Y
                              750
GGGACACCTTCACGTGGGACCCCAGGACTGCCAGCCTTGCCCAGTGCGACCAGCCTGCAGCCCTACTGCCACCTCACTGATGGA
 G  T  P  S  R  G  T  P  G  D ©Q  P ©A ©P  L  S  I  D  S  N  N  F  S  P  T ©H  L  T  D  G

GAGGAAGTGGTTTGTGAC   2520
 E  E  V  V ©D
                                            790
CAATGTGCCCCGGGTTACTCAGGATCCTGGTGTGAGAGATGTGCAGATGGTTACTACGGTAACCCCAACCGTGCCAGGGGAACCTGTACCATGCAACTGC
 Q ©A  P  G  Y  S  G  S  W ©E  R ©A  D  G  Y  Y  G  N  P  T  V  P  G  G  T ©V  P ©N ©

AGTGGCAATGTTGATCCC   2640
 S  G  N  V  D  P
                                                                    830
TTGGAGGCTGGCCACTGTGACTCTGTCACGGGGAATGCTGAAGTGCTTATGAACACAGACGGTGCCCATTGTGAGAGGTGTGCAGATGGCTTCTATGGA
 L  E  A  G  H ©D  S  V  T  G  E ©L  K ©L  W  N  T  D  G  A  H ©E  R ©A  D  G  F  Y  G

GATGCCGTGACTGCCAAA   2760
 D  A  V  T  A  K
                                                                  870
AACTGCCGAGCTGTGACTGCCACGAGAATGGCTCTCCCTTTCGCGTCTGCCATCTGGAGACTGGACTGTGACTGCAAACCTCACGTGACAGGACAGCAG
 N ©R  A ©D ©H  E  N  G  S  L  S  G  V ©H  L  E  T  G  L ©D ©K  P  H  V  T  G  Q  Q

TGTGACCAGTGCCTGTCT   2880
©D  Q ©L  S
```

FIG.4-5

```
                                890                          900                          910
GGCTACTACGGGTTGGACACGGGTTGGCTTGCTGTGCCCCTGTAACTGCAGTGTGGAAGGCTCTGTATCTGACAACTGCACGGAGGAAGACAGTGTCACTGT
 G  Y  Y  G  L  D  T  G  L  G  Ⓒ  V  P  Ⓒ  N  S  V  E  G  S  V  S  D  N  Ⓒ  T  E  E  G  Q  Ⓒ  H  Ⓒ
GGACCAGGTGTCTCTGGG      3000
 G  P  G  V  S  G
                                930                          940                          950
AAACAGTGTGACAGTTGTTCACATGGTTTCTATGCATTCCAGGATGGCGGCTGCACACCCTGTGACTGCTCATACCCAGAATAACTGTGACCCGCCTCT
 K  Q  Ⓒ  D  R  Ⓒ  S  H  G  F  Y  A  F  Q  D  G  G  Ⓒ  T  P  Ⓒ  D  Ⓒ  A  H  T  Q  N  N  Ⓒ  D  P  A  S
GGAGAGTGTCTCTGCCCG      3120
 G  E  Ⓒ  L  Ⓒ  P
                                970                          980                          990
CCTCACACGCAGGGCTGAAGTGTGAGGAGTGTGAAGAGGCATACTGGGGTCTGGACCCAGAGCAGGGTGCCAGGCTTGCAATTGCAATGCAGTGTGGGCTCC
 P  H  T  Q  G  L  K  Ⓒ  E  E  Ⓒ  E  E  A  Y  W  G  L  D  P  E  Q  G  Ⓒ  Q  A  Ⓒ  N  Ⓒ  S  A  V  G  S
ACGAGTGCCCAGTGTGAT      3240
 T  S  A  Q  Ⓒ  D
                                1010                         1020                         1030
GTTCTCTGGCCACTGCCCTGCCCCTGCAAAAAAGGGGTTTGGTGGGCCAGAGCTGCCATCAGTGTTCCTTAGGCTACAGAAGTTTCCTCCTGACTGTGTCCCCTGTGGC
 V  L  S  G  H  Ⓒ  P  Ⓒ  K  K  G  F  G  G  Q  S  Ⓒ  H  Q  Ⓒ  S  L  G  Y  R  S  F  P  D  Ⓒ  V  P  Ⓒ  G
TGTGACCTGAGGGGACA       3360
 Ⓒ  D  L  R  G  T
                                1050                         1060                         1070
CTGCCTGACACCTGTGACCTGGAACAGGGTCTCTGCAGCTGTCCTGCAAGGAGAATCTCTGGGCCCCAGTGCAGTAAG
 L  P  D  T  Ⓒ  D  L  E  Q  G  L  Ⓒ  S  Ⓒ  S  E  D  S  G  T  Ⓒ  S  Ⓒ  K  E  N  V  G  P  Q  Ⓒ  S  K
TGCCAAGCCGGCACCTTT      3480
 Ⓒ  Q  A  G  T  F
                                1090                         1100                         1110
GCCTTGCGAGGGGACAACCCTCAAGGCTGCAGCCCTTGCTTCTTCGGTTTGTCTCAGCTCTGCTCAGAGTTGGAGGGTTACGTGAGGACTCTGATAACT
 A  L  R  G  D  N  P  Q  G  Ⓒ  S  P  Ⓒ  F  F  G  L  S  Q  L  Ⓒ  S  E  L  E  G  Y  V  R  T  L  I  T
CTAGCCTCCGATCAGCCC      3600
 L  A  S  D  Q  P
```

FIG.4-6

```
              1130                                        1140                                        1150
CTCCTGCATGTGGTTTCACAGAGCAACCTCAAGGGCACAATCGAAGGCGTGCATTTCCAGCCTCCTGACACCTTGCTGGACGCAGAGGCTGTCCGCCAGCAT
 L  L  H  V  V  S  Q  S  N  L  K  G  T  I  E  G  V  H  F  Q  P  P  D  T  L  L  D  A  E  A  V  R  Q  H
ATCTATGCAGAGCCATTT    3720
 I  Y  A  E  P  F
              1160                                        1170                                        1180                                   1190
TACTGGCGGCTACCAAAGCAGTTCCAGGGAGACCAGCTCTTGGCCTATGGTGGGAAACTCCAGTACAGTGTGGCTTTCTACTCTACACTTGGCACCGGAACA
 Y  W  R  L  P  K  Q  F  Q  G  D  D  Q  L  L  A  Y  G  G  K  L  Q  Y  S  V  A  F  Y  S  T  L  G  T  G  T
TCCAATTATGAGCCTCAA    3840
 S  N  Y  E  P  Q
              1200                                        1210                                        1220                                   1230
GTCCTCATCAAAGGAGGTCGGGCCAGGAAGCACGTCATTTATATGGATGCCCCAGCCTGAGAATGGAGTGAGACAGGATTACGAAGTGCAGATGAAAGAG
 V  L  I  K  G  G  R  A  R  K  H  V  I  Y  M  D  A  P  A  P  E  N  G  V  R  Q  D  Y  E  V  Q  M  K  E
GAATTCTGAAATATTTT    3960
 E  F  W  K  Y  F
              1240                                        1250                                        1260                                   1270
AACTCCGTGTCTGAGAAACACGTCACACACTCTGATTTTATGTCTGTTCTCAGCAATATTGACTACATCCTCATCAAAGCATCATACGGCCAGGACTCCAG
 N  S  V  S  E  K  H  V  T  H  S  D  F  M  S  V  L  S  N  I  D  Y  I  L  I  K  A  S  Y  G  Q  G  L  Q
CAGAGCAGAATTGCCAAC    4080
 Q  S  R  I  A  N
              1280                                        1290                                        1300                                   1310
ATTTCCATGGAGGTTGGCCGGAAAGCTGTCGAGCTGCCCGCTGAGGGCGAGGCAGCACTTCTGGAGCTCTGTGTCTGAGCTCTGTCTCCTGCACCGCCAGGACAC
 I  S  M  E  V  G  R  K  A  V  E  L  P  A  E  G  E  A  A  L  L  E  L  V  P  P  G  T  A  G  H
TCCTGTCAGGACTGTGCT    4200
 S  Q  Q  D  A
              1320                                        1330                                        1340                                   1350
CCTGGGTACTACAGAGAAAAGCTCCCAGAAGTGGCAGGGAGGCGGCCCCGCCCGCCCTCTGCTGGCTCCTGCAATTGCCCTGCCCCAGTGGGAGTCCTGGTGCTGCCAGTGATGTC
 P  G  Y  Y  R  E  K  L  P  E  S  G  R  G  P  R  P  L  L  A  P  V  P  N  N  H  S  D  V
TGTGACCCCGAAACTGGA    4320
 D  P  E  T  G
                1360
```

FIG.4-7

```
                    1370                              1380                              1390
AAGTGCCTGAGCTGCAGGGACCACACATCCGGGGACCACTGTGAGCTGTGTCTTCTGTGCTTCTGGCTACTATGGGAAGGTGACTGGACTGCCTGGAGACTGTACCCCG
 K  C  L  S ©  R  D  H  T  S  G  D  H  C  E  L ©  A  S  G  Y  Y  G  K  V  T  G  L  P  G  D © T  P
TGCACCTGTCCTCATCAC                                                                              4440
©  T © P  H  H
                    1410                              1420                              1430
CCTCCTTCAGTTCAGCCCCACTTGTGTCGTGGAAGGTGACAGTGATTTCCGGTGCAATGCCCTGCCTCCCGGCTATGAAGGACAGTACTGTGAAAGGTGC
 P  P  F  S  F  S  P  T ©  V  V  E  G  D  S  D  F  R © N  A © L  P  G  Y  E  G  Q  Y © E  R ©
TCTGCAGGCTATCACGGC                                                                              4560
 S  A  G  Y  H  G
                    1450                              1460                              1470
AACCCTCGAGCAGCAGGTGTAGCTGCCAAAGGCTCTGTCCACAGTGATTGCAACCCCCAAGGCTCTGTCCACAGTCATCCGGGCAGTGTGTCTGCAAG
 N  P  R  A  A  G  G  S ©  Q  T ©  D © N  P  Q  G  S  V  H  S  D © D  R  A  S  G  Q © V © K
CCAGGAGCTACACGGC                                                                                4680
 P  G  A  T  G  L
                    1490                              1500                              1510
CACTGTGAGAAATGCCTGCCAGACACATCCTGAGAGCGACTGTGTTTCCTGATGATGACTGTGTGGGTCCTTTGCTGAACGACCTGGATTCTGTT
 H © E  K © L  P  R  H  I  L  M  E  S  D © V  S © D  D  D  D © V  G  P  L  L  N  D  L  D  S  V
GGTGATGCCGTTCTGTCT                                                                              4800
 G  D  A  V  L  S
                    1530                              1540                              1550
CTGAACCTCACGGGCGTTCCCCTGCTCCCTATGCCCTGCTCCCTATGAAATCTGAATAATATTTCCAGAGGTATTAATAAGGAAAATGCCAAG
 L  N  L  T  G  V  S  P  A  P  Y  G  I  L  E  N  L  E  N  T  T  K  Y  F  Q  R  Y  L  I  K  E  N  A  K
AAGATTCGAGCAGAGATC                                                                              4920
 K  I  R  A  E  I
                    1570                              1580                              1590
CAGCTCGAAGGGATTGCAGAGACAGAACAAAATCTGCAAAAGGAGCTCACCAGAGTCTTAGCACGCCATCAGAAGGTGAACGCTGAAATGGAAAGAACTTCC
 Q  L  E  G  I  A  E  Q  T  E  N  L  Q  K  E  L  T  R  V  L  A  R  H  Q  K  V  N  A  E  M  E  R  T  S
AATGGGACTCAAGCCCTG                                                                              5040
 N  G  T  Q  A  L
```

FIG.4-8

```
                                1610                       1620                        1630
GCCAGGTTCATTGAGCAGCTACATGCAAACATCAAAGAAATCACAGAAAAGGTGGCAACGTTGAACCAGAGGGCGCGTAAAGATTCCAGCCACCCGTGTCT
 A  T  F  I  E  Q  L  H  A  N  I  K  E  I  T  E  K  V  A  T  L  N  Q  T  A  R  K  D  F  Q  Q  P  P  V  S
            1640
GCCCTTCAGAGCATGCAC        5160
 A  L  Q  S  M  H
                                1650                        1660                        1670
CAGAACATTTCGTCTCTGCTGGACTCATCAAGGAAAGGAATTTCACAGAGATGCAGCAGAATGCTACCCTTGAGCTCAAGGCTGCTAAAGACTTATTGTCA
 Q  N  I  S  L  L  G  L  I  K  E  R  N  F  T  E  M  Q  Q  N  A  T  L  E  L  K  A  A  K  D  L  L  S
            1680
CGGATTCAGAAAAGGTTT        5280
 R  I  Q  K  R  F
                                1690                         1700                         1710
CAGAAGCCTCAGGAAAAGTTGAAGGCATTGAAGGAGGCCAACAGCCTCCTTTCCAACCACAGTGAAAAACTGCAGGCTGCTGAGGAGCTCCTTAAGGAAGCT
 Q  K  P  Q  E  K  L  K  A  L  K  E  A  N  S  L  L  S  N  H  S  E  K  L  Q  A  E  E  L  L  K  E  A
            1720
GGAAGCAAGACCCAGGAG        5400
 G  S  K  T  Q  E
                                1730                         1740                         1750
AGCAACCTCCTGCTCCTTGTCAAGGCCAACCTGAAGGAATTCCAGGAGAATTCCAGGAGAACAAAATGTGACCTCAGAGCTCATT
 S  N  L  L  L  L  V  K  A  N  L  K  E  E  F  Q  E  K  K  L  R  V  Q  E  E  Q  N  V  T  S  E  L  I
            1760
GCCAAGGGTAGAGAATGG        5520
 A  K  G  R  E  W
                                1770                         1780                         1790
GTGGATGCTGCCGGGACTCACACAGCTGCTGCACAAGACACCCTAACACAGCTGGAGCATCACCGAGATGAACTCCTTCTGTGGGCCAGAAAAATCAGGAGC
 V  D  A  A  G  T  H  T  A  A  A  Q  D  T  L  T  Q  L  E  H  H  R  D  E  L  L  L  W  A  R  K  I  R  S
            1800
CACGTAGATGACCTCGTC        5640
 H  V  D  D  L  V
                                1810                         1820                         1830
ATGCAGAGTCCAAACGAGAGCCCGTGACCTGTTCCACAGGGCAGAGCAGGCATGCCTCGAGCTGCAGAGCAGGGCAGGAGCTTTGGACAGAGACCTTGAA
 M  Q  M  S  K  R  R  A  R  D  L  V  H  R  A  E  Q  H  A  S  E  L  Q  S  R  A  G  A  L  D  R  D  L  E
            1840
AATGTTAGAAACGTGTCT        5760
 N  V  R  N  V  S
```

FIG. 4-9

```
                                       1850                                      1870
TTGAATGCCACCAGTGCGGCACACGTCCACAGCAACATCCAGACAACACTGACAGAGGAAGCTGAGATGCTGGCTGCTGATGCTCACAAGACGGCGAATAAGACA
 L  N  A  T  S  A  A  H  V  H  S  N  I  Q  T  L  T  E  E  A  E  M  L  A  A  D  A  H  K  T  A  N  K  T
                   1880
GACTTGATCTCCGAATCC   5880
 D  L  I  S  E  S
                                       1890                                     1910
CTGGCTTCTCGGGGGAAGCAGTCCTTCAGCGCTCGTCTCCGGTTTCTAAAGGAAAGTGTCGGTACCAGGAAGCAGCAAGGCATTACGATGAAGCTGGAT
 L  A  S  R  G  K  A  V  L  Q  R  S  S  R  F  L  K  E  S  V  G  T  R  R  K  Q  Q  G  I  T  M  K  L  D
                   1920
GAGTTGAAAAACTTAACG   6000
 E  L  K  N  L  T
                                       1930                                     1950
AGTCAATTTCAGGAGAGCGTGGATAACATTACGAAGCAGGCCAACGACTCCCTTGCGATGCTTAGAGAAAGCCCTGGAGGTATGAGAGAAGGCAGGAAA
 S  Q  F  Q  E  S  V  D  N  I  T  K  Q  A  N  D  S  L  A  M  L  R  E  S  P  G  G  M  R  E  K  G  R  K
                   1960
GCCAGAGAGCTGGCGGCA   6120
 A  R  E  L  A  A
                                       1970                                     1990
GCAGCCAACGAGAGTGCGCTGAAGACACTGGAGCATGTGCTGGCTTTGAGCCTGAGGGTCTTCAATACATCAGAGGACCTGTCCAGAGTGAATGCCACAGTC
 A  A  N  E  S  A  V  K  T  L  E  D  V  L  A  L  S  L  R  V  F  N  T  S  E  D  L  S  R  V  N  A  T  V
                   2000
CAGGAGACAAACGACCTT   6240
 Q  E  T  N  D  L
                                       2010                                     2030
CTGCATAACTCCACGATGACCACTCTCTTGGCTGGAAGAAAAATGAAGGACATGGAAATGCAAGCCAACCTTTTATTGGATCGATTGAAACCTTTGAAACC
 L  H  N  S  T  M  T  T  L  L  A  G  R  K  M  K  D  M  E  M  Q  A  N  L  L  L  D  R  L  K  P  L  K  T
                   2040
CTGGAGGAGAACCTGAGC   6360
 L  E  E  N  L  S
                                       2050                                     2070
AGAAACCTGTCGGAGATCAAGCTGCTGATCAGCCGGGCCCGAAAACAAGGCGGCGTCGCATCAAAGTCGCCGTGTCTCGAGACAGACTGCATCCGCCCTAT
 R  N  L  S  E  I  K  L  L  I  S  R  A  R  K  Q  A  A  S  I  K  V  A  V  S  A  D  R  D  Ⓒ  I  R  A  Y
                   2080
CAGCCCTCAGACTTCATCT   6480
 Q  P  Q  T  S  S
```

FIG.4-10

```
ACCAATTACAACACCTTGATCCTGAACGTGAAGACGGCAGGAGCCCGACAACCTCCTCTGGCAGCAGCAGCAGTTCTGACTTTCTCGCAGTGGAG
 T  N  Y  N  T  L  I  L  N  V  K  T  Q  E  P  D  N  L  L  F  Y  L  G  S  S  S  S  D  F  L  A  V  E
                         2090                    2100                    2110
ATGGGCGGGGAAGGTC  6600
 M  R  R  G  K  V
2120
GCCTTTCTGGGACCTGGGGTCCGGGTCCAAGGTTGGAATTCCCAGAGGTCTCCACAAGGTTGGAATTCCCAGAGGTCTCCATCAATAACAACAGATGGCACAGCATCTACATAACCAGGTTTGA
 A  F  L  W  D  L  G  S  G  S  T  R  L  E  F  F  P  E  V  S  I  N  N  N  R  W  H  S  I  Y  I  T  R  F  G
          2130                    2140                    2150
AACATGGGGTCCCTGAGT  6720
 N  M  G  S  L  S
2160
GTAAAGGAAGCAAGCCTCGCCGAGAACCCACCGGTCAGGACCGTCGAAGGTTCTGGACATAAACAATTCAACGCTGATGTTTGTT
 V  K  E  A  S  A  A  E  N  P  P  V  R  T  S  K  S  P  G  P  P  S  K  V  L  D  I  N  N  S  T  L  M  F  V
2170                    2180                    2190
GGAGGGCTCGGAGGTCAG  6840
 G  G  L  G  G  Q
2200
ATCAAGAAATCCCCGGCTGTGAAGGTTACTCATTTTAAGGGCTGCATGGGAGAGGCCTTCTTGAATGGCAAATCGATTGGCCTGTGGAATTACATCGAGAGA
 I  K  K  S  P  A  V  K  V  T  H  F  K  G  C  M  G  E  A  F  L  N  G  K  S  I  G  L  W  N  Y  I  E  R
2210                    2220                    2230
GAGGGGAAGTGCAATGGC  6960
 E  G  K  C  N  G
2240
TGCTTTGGAAGCTCCCAGAACGAAGATTCCTCCTTCCATTTCGATGGAAGCGGGTACGCCATGGTGGAGAAGACGCTCCGCCACCGTGACGCAGATAGTA
 C  F  G  S  S  Q  N  E  D  S  S  F  H  F  D  G  S  G  Y  A  M  V  E  K  T  L  R  P  T  V  T  Q  I  V
                2250                    2260                    2270
ATTCTCTTCAGCACCTTC  7080
 I  L  F  S  T  F
2280
TCCCCGAATGGCCTTCTTTTTTACCTGGCTTCAAACGGCACCAAGGACTTCCTATCCATCGAGCTGGTCCGTGGCAGGGTCAAAGTGATGTGACCTAGG
 S  P  N  G  L  L  F  Y  L  A  S  N  G  T  K  D  F  L  S  I  E  L  V  R  G  R  V  K  V  M  V  D  L  G
2290                    2300                    2310
TCAGGACCCCTCACTCTT  7200
 S  G  P  L  T  L
2320
```

FIG.4-11

```
ATGACAGACAGGCGGGTATAACAACGGAACCTGGTATAAAATCGCCTTCCAGCGAAACCGGAAGCAAGGACTGCTAGCTGTCTTCGATGCATATGACACCAGT
 M  T  D  R  R  Y  N  N  G  T  W  Y  K  I  A  F  Q  R  N  R  K  Q  G  L  L  A  V  F  D  A  Y  D  T  S
              2330                2340                2350

GACAAGGAGACAAAGCAA    7320
 D  K  E  T  K  Q
        2360

GGAGAGACTCCAGGAGCCGCTTCCGACCTCAATCGGCTGGAGAAAGACCTGATTATCGTGGGTGGATTGCCTCATTCTAAGGCTGTGAGGAAAGGGGTCAGC
 G  E  T  P  G  A  A  S  D  L  N  R  L  E  K  D  L  I  Y  V  G  G  L  P  H  S  K  A  V  R  K  G  V  S
              2370                2380                2390

AGCAGAAGCTATGTGGGC    7440
 S  R  S  Y  V  G
        2400

TGTATCAAGAACCTAGAGATATCCAGGTCCACCTTTGATTGCTGAGAAATTCCTACGGAGTGAGAAAGGCTGCGACTGAGCCTATCCAGAGTGTGAGT
 C  I  K  N  L  E  I  S  R  S  T  F  D  L  L  R  N  S  Y  G  V  R  K  G  A  L  E  P  I  Q  S  V  S
              2410                2420                2430

TTCCTGAGAGGGCTAT    7560
 F  L  R  G  G  Y
        2440

GTGGAGATGCCACCCAAGTCTCTCACCTGAGTCATCCGAGTCCCTGCTGGCCACATTCGCCACCAAGAACAGCGGAATCCTCCTGGTTGCCCTGGGCAAGGAT
 V  E  M  P  P  K  S  L  S  P  E  S  S  L  L  A  T  F  A  T  K  N  S  G  I  L  L  V  A  L  G  K  D
              2450                2460                2470

GCGGAGGAGGCTGGTGGG    7680
 A  E  E  A  G  G
        2480

GCTCAGGCACATGTGCCCTTCTTTTTCCATCATGCTGCTTGAGGGACCAGTCATGTCAACTCTGAAGTGCATCGAAGTCCATGTGAACAGTGGAGATGGCACCAGTCTGAGGAAGGCCCTCCTG
 A  Q  A  H  V  P  F  F  S  I  M  L  L  E  G  R  I  E  V  H  V  N  S  G  D  G  T  S  L  R  K  A  L  L
              2490                2500                2510

CATGCCCCCACCGGCTCC    7800
 H  A  P  T  G  S
        2520

TACAGTGATGGACAGGAGAACACTCCATCCCCTGGTTAGGAATCGGAGAGTTATCACCATACAAGTGGATGAGAACAGTCCCTAGAAATGAAGTTGGCTCCA
 Y  S  D  G  Q  E  H  S  I  S  L  V  R  N  R  R  V  I  T  I  Q  V  D  E  N  S  P  V  E  M  K  L  G  P
              2530                2540                2550

TTAACAGAAGGAAAGACG    7920
 L  T  E  G  K  T
        2560
```

FIG.4-12

```
                      2570                 2580                 2590
ATCGACATATCCAACCTGTACATAGGGGGACTTCCGGAGGACAAGGCCACCCCCATGCTCAAGATGCGACTTCGTTCCATGGGTGTATTAAAACGTGGTC
 I  D  I  S  N  L  Y  I  G  G  L  P  P  E  D  K  A  T  P  M  L  K  M  R  T  S  F  H  G  Ⓒ  I  K  N  V  V
CTTGACGCTCAACTTTG    8040
 L  D  A  Q  L  L
                      2610                 2620                 2630
GACTTCACCCATGCGACTGGCTCTGAGCAAGTAGAGCTTGCTGGCAGAAGAGCCATGCAGAGTCTGCACAGAGAACACGGGGAACTCCCT
 D  F  T  H  A  T  G  S  E  Q  V  E  L  D  T  Ⓒ  L  L  A  E  E  P  M  Q  S  L  H  R  E  H  G  E  L  P
CCGGAGCCCCCAACTCTA    8160
 P  E  P  P  T  L
                      2650                 2660                 2670
CCACAGCCTGAACTGTGCCAGTAGACACGGCTCCGGGTATGTGGCCAGTGCTCACCAGTTTGGCCTCTCGCAGAACAGCCACTTGGTCTCCCTCTGAAT
 P  Q  P  E  L  Ⓒ  A  V  D  T  A  P  G  Y  V  V  A  G  A  H  Q  F  G  L  S  Q  N  S  H  L  V  L  P  L  N
CAGTCTGATGTCCGGAAG    8280
 Q  S  D  V  R  K
                      2690                 2700                 2710
AGGCTCCAGGTGCAGCTGAGCTGAGCATTCGGACATTGCCTCCAGTGGCCTCATTTACTATGTGGCTCATCAGAACCAAATGGACTACGCCACGCTCCAGCTCCAA
 R  L  Q  V  Q  L  S  I  R  T  F  A  S  S  G  L  I  Y  Y  V  A  H  Q  N  Q  M  D  Y  A  T  L  Q  L  Q
GAGGGCCGCCTGCACTTC    8400
 E  G  R  L  H  F
                      2730                 2740                 2750
ATGTTTGATCTCGGCAAGGGCCGGACCAAGGTCTCCCACCCTGCCCTGCTCAGTGATGGCAAGTGGCACACAGTCAAGACACAGAATACATTAAAGGAAGGCG
 M  F  D  L  G  K  G  R  T  K  V  S  H  P  A  L  L  S  D  G  K  W  H  T  V  K  T  E  Y  I  K  R  K  A
TTCATGACTGTTGACGGC    8520
 F  M  T  V  D  G
                      2770                 2780                 2790
CAAGAGTCCCCAGTGTGACTGTGGTGGCAATGCAACCACGCTGGATGTGAAAGGAAACTGTACCTCGGAGGCCTTCCCAGCCACTACAGGGCCAGGAAC
 Q  E  S  P  S  V  T  V  V  G  N  A  T  T  L  D  V  E  R  K  L  Y  L  G  G  L  P  S  H  Y  R  A  R  N
ATCGGGACTATCACCCAC    8640
 I  G  T  I  T  H
```

FIG.4-13

```
         2810                              2820                              2830
AGCATCCCTGCCTGCATTGGGAATCATGGTTAATGGCCAACAGCTGGATAAAGACAGGCCCTTGTCTGCCTCTGCTGTGGACAGGTGCTATGTCTGCT
 S  I  P  A ©I  G  E  I  M  V  N  G  Q  Q  L  D  K  D  R  P  L  S  A  S  A  V  D  R ©Y  V  V  A
                 2840
CAGGAAGAACTTTCTTT    8760
 Q  E  G  T  F  F
                             2850                              2860                              2870
GAAGGAAGCGGATATGCAGCTCTTGTCAAGGAAGTTACAAAGTTCGATTGGATTTAAATATCACACTGGAGTTCCGTACTACCTCTAAGAATGGCGTCCTC
 E  G  S  G  Y  A  A  L  V  K  E  G  Y  K  V  R  L  D  L  N  I  T  L  E  F  R  T  T  S  K  N  G  V  L
                                                                   ‾‾‾‾‾‾‾‾‾‾‾‾‾‾
CTGGAATCAGCAGTGCC    8880
 L  G  I  S  S  A
             2890                              2900                              2910
AAAGTGGATGCCATTGGCCTAGAGATTGTAGATGGCAAGGTCTTATTTCACGTCAACAACGGTGCCGAAGGATAACAGCCACCTACCAGCCCAGAGCCGCC
 K  V  D  A  I  G  L  E  I  V  D  G  K  V  L  F  H  V  N  N  G  A  G  R  I  T  A  T  Y  Q  P  R  A  A
                         2920
AGAGCTCTCTGTGATGGC    9000
 R  A  L ©D  G
                 2940                              2950
AAGTGGCACACACTCCAAGCCCCACACAAAAGCAAGCACCGCATCGTCCTGACTGTGGACGGGAATTCCGTTAGGGCTGAAAGCCCCACACCATTCCACCTCG
 K  W  H  T  L  Q  P  A  H  I  K  Q  N ©L  S  S  R  A  S  F  R  G ©V  R  N  L  R  L  S  R  G  S
             2960
GCAGACACCAACGATCCC    9120
 A  D  T  N  D  P
                             2970                              2980                              2990
ATTTATGTGGTGGCTATCCTGCCCACATCAAACAGAAGAGTCTTCCCTCATTCCTGCCCGGGCCGCTGTGTGAGGAACCTCAGGCTGAGCAGGGCTCA
 I  Y  V  G  G  Y  P  A  H  I  K  Q  N ©L  S  S  R  A  S  F  R  G ©V  R  N  L  R  L  S  R  G  S
                 3000
CAAGTGCAGTCCTTGGAC    9240
 Q  V  Q  S  L  D
                             3010                              3020                              3030
CTGAGCCGAGCCTTTGACTTACAAGGAGTCTTCCCTCATTGCCATCTCAGGTTATGTTTCCAGAGGAAAATGCTGTATTTATGTTGAACTAAAGCCACACGGAC
 L  S  R  A  F  D  L  Q  G  V  F  P  P  H  S ©P  G  P  E  P  *
                     3040
ATGGAAGAGAGCAGTTTG    9360
                                 3050                              3060
TGAACTCAAGCAGTCAGCTCCAGTCCCATTCCCATCCCATTGCCATCTCAGGTTATGTTTCCAGAGGAAAATGCTGTATTTATGTTGAACTAAAGCCACACGGACA
ACAGATACCTCTATTAAA    9480
TGGTTTAAACGTCAGTGGAATTAAAAAAAAAAAAAAAA    9520
```

```
A  [IVb]  VTDLMST-N-KIRSQQDVLG-GHRQISINNTAVMQRL-TSTYYWAAPEAYLGNKLTAFGGFLKYTVS-YDIPV    580
A  [IVg]  LLHVVSQSNLKGTIEG-VHFQPPDTLLDA-EAYRQHIYAEPFYWRLPKQFQGDQLLAYGGKLQYSVAFYSTLG   1231
B2 [IVj]  DI--AVISDSYF-PRYFIAPVKFLGNQVLSYGQNLSFSFRV-DRRD                              552

A  [IVb]  ETVDSDLMSHADIIIKQNGL-----TISTRAEGLSLQPYEEYFNVVRLVPENFRD-FNT-R-REIDR-DQLMT   644
A  [IVg]  -TGTSNYEPQV--LIKG-G-MARKHVYMDAPENGVRQDYE--YQM-KEEFWKYFNSVSEKHVTHSD-FMS     1295
B2 [IVj]  -TRLSA-EDLV--LE-QAQLMVSVPLIAQGNSYPSETTVK--YI--FRL-HEAT-DY-PWRPA--LSPFE-FQK   611

A  [IVb]  VLAMVTHLLIRANYNSAKMALYRLDSYSLDIASPNAIDL-AV--AA                             687
A  [IVg]  VLSHIDYILIKASYGQG-LQQSRIANISMEVGR-KAVELPAEGEAA                            1339
B2 [IVj]  LENNLTSIKIRGTY-SERTAGY-LDDVTLQSARPGPG-VPAT                                 650
```

FIG. 9

```
                                                                                              61
             AMDECADEGGRPQRCM-P-EFVNAAFN-VTV-YATNICQTP--PEEYC--VQTGVTG--VTKS-CHLCQAGQ         62
B2                                                                                            55
B1  QEPEFSYGCA-EG---SCY-PATGDLLIGRAQKLSV-TSTCCLHK-PEPYCI-VSHL--QE-DKK-CFICDSRD-GN
A              QQRGLFPA-ILNLATNA-HIS-ANATCGE-KGPEMFCKLVEH-YPGRPVRHAQCRVCD-GN

124
B2  Q-H--LQHGAAFL------TDYN-NQADIT-WWQSQTMLAGVQYPNSINLTLHEGKA-EDITYVRLK--FHTSRPES             126
B1  PYHE-LNPDS-HL-IENVVTFAPNRLK--IWWQSEN---GVE--NVT-IQLDEE-AEFHFT-HLI-MTEKT-FRFAA             117
A   S---T-NPRERHPI-----SH----AIDGTNNWWQSPSIQNGREYHWVT-VTLEDLRQV-FQVAYIIEKAANA-PRPGN

187
B2  FA-IYKRTRED-GP--WIPYQTT---SGS--CENT-YSKAN--RGFIRTGG--D-EQQALCTDEF-SDISPLT--GGNVAF-        187
B1  ML-IERSS-DFG--KTMGVTRYFAY-D--CESSFPGIST--CPMK-KV-DD----IIC-DSRYSDIEPSIE-GEVIFR            182
A   W-ILERSV-D-GVKFK-PWQYYAVSDTECL--TRYKITPRRGPP-TYRADNE--VICT-SYYSKLVPL-EHGE-IHT

249
B2  STLE-GRPSAYNF-DN-SPVLQEWVTA-TDIRVTENRLENTFG-DEVFNEPK-VLKS------YYYAISDFAVGG               248
B1  -ALD--P-AFKIEDPYSPRIQ-NLLKITNLRIKFVKLHTLG-DNLLD-S-RM-EIREK---YYAVYDMVVRG                  251
A   S-LINGRPSAD---DP-SPQLLEFTSARY-IRLREQRIRTENAD-LMTLSHRDERDLDPIVTRRY-YSIKBISVGG
```

FIG. 17A

FIG. 18A

FIG. 25 INHIBITION OF PC12 NEURITE FORMATION BY ANTISERA TO LAMININ SYNTHETIC PEPTIDES — LAMININ, ANTI P1-B1, BLANK, ANTI P10-A

LAMININ A CHAIN DEDUCED AMINO ACID SEQUENCE, EXPRESSION VECTORS AND ACTIVE SYNTHETIC PEPTIDES

FIELD OF THE INVENTION

The present invention relates to the Laminin A chain deduced amino acid sequence, expression vectors and active synthetic peptides. In addition, the invention is directed to antibodies raised against the synthetic peptides and to pharmaceutical compositions containing one or more of the synthetic peptides.

BACKGROUND OF THE INVENTION

Laminin is a large (M.wt=800,000) glycoprotein which is localized to basement membranes, the thin extracellular matrix which separates epithelium from the underlying stroma. Laminin ($M_r$ 900,000) is composed of three chains, A ($M_r$=400,000), B1 ($M_r$=210,000) and B2 ($M_r$=200,000) which are joined by disulfide bonds to form a cruciform-like structure (see FIG. 1). FIG. 1 shows a schematic Model of the laminin molecule. The roman numerals and α indicate the structural domains. Laminin is of special interest because it has multiple biological activities including promoting cell adhesion, migration, growth, cell differentiation, phagocytosis, collagenase production, tumor cell invasion, and neurite outgrowth. It also binds to many other materials including collagen IV, heparin, heparan sulfate proteoglycan, and entactin. Using proteolytic fragments of laminin, an active site for cell adhesion was proposed to be contained within a large complex formed by the intersection of the three chains. A second active site for cell adhesion and for neurite outgrowth was localized to a region near the end of the long arm. Recently we have identified an active site on the B1 chain near the intersection of the 3 chains. A pentapeptide from the B1 chain sequence (YIGSR) promotes cell adhesion, cell mirgration, receptor binding and reduces tumor metastases in vivo. The abbreviations for amino acids are shown below.

| Abbreviations for amino acids | | |
|---|---|---|
| Amino acid | Three-letter abbreviaton | One-letter symbol |
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Likewise, the peptide reduces neural crest cell outgrowth from notochord, prevents endothelial cell differentiation, and delays myoblast fusion. It does not promote cell growth, increase collagenase release or promote neurite outgrowth suggesting that these activities lie within another site(s) in laminin.

We have recently cloned and sequenced all of the mouse B1 and B2 chains. Here, we present the isolation and sequence of cDNA clones spanning 9520 bases which encode the entire A chain of mouse laminin. The nucleotide sequence of the clones contains an open reading frame of 3084 amino acids including 24 amino acids of a signal peptide. The A chain contains some eight distinct domains including α-helices, cysteine-rich repeats and globules.

Accordingly, we have completely cloned and sequenced the A chain of laminin, prepared vectors which express portions of the sequence and identified active peptides. One peptide (PA22-2) is active for cell adhesion, cell growth, haparin binding, neurite outgrowth, collagenase production, cell migration, and increases tumor metastasis and inhibits endothelial cell differentiation. The other peptide (PA21) promotes endothelial cell adhesion and neurite outgrowth. Possible commercial and medical applications include uses as an adhesion and regeneration agent for nerve guides and as an adhesion agent for vascular protheses. The peptide may also be used in wounds and as a control for blood vessel formation. The active peptides have wide usage in research, nerve regeneration and in cancer treatment.

Laminin was first isolated in this laboratory (JBC 254:9933, 1979) and one year later its ability to promote cell attachment was determined here (Cell 22:719, 1980). The entire primary peptide sequence of the three chains was determined from cDNA cloning here. Using synthetic peptides and their corresponding antibodies specific for the B1 chain, we previously identified two active sites of 5 amino acids each which promote cell adhesion, migration, receptor binding and inhibit tumor cell metastases (Graf et al, *Cell* 48:989, 1987; Graf et al, *Biochemistry* 26:6896, 1987, Iwamoto et al, Science, 238:1132, 1987, Iwamoto et al, *J. Cellul. Physiol.* 134:287, 1988 and patent application #7-013,919 which is herein incorporated by reference). We now have recently constructed various vectors in bacterial and mammalian cells which express portions of the A chain protein. We have also identified two active peptides which have some of the biological activities of laminin peptide PA22-2 having 19 amino acids and which promotes cell adhesion, neurite outgrowth, collagenase production, tumor metastases and competitively interferes with endothelia cell differentiation. The second peptide PA21 is 12 amino acids long and it promotes the adhesion of endothelial cells very strongly and has weak activity with other cells. It has neurite outgrowth promoting activity with some neuronal cells when coupled to albumin or transferrin, and can disrupt endothelial cell differentiation.

SUMMARY OF THE INVENTION

One object of the present invention is to provide a DNA sequence of cDNA clones coding for the entire A chain of mouse laminin which has a variety of biological activities.

Another object of the present invention is to provide a probe using this sequence. The method involves screening a human cDNA library using the mouse sequence as a probe. A clone with a cross-hybridizable sequence in plaque is purified and the DNA isolated therefore, subcloned and subjected to DNA sequence analysis. Thus, another object of this invention is to produce a human laminin A chain by this method.

A further object of the invention is to provide a vector containing a DNA sequence as described above in association with an expression regulatory sequence. Such a vector may be employed in a process for producing the A chain of laminin or any portion of it. This process may employ a number of known cells as host cells for expression of the polypeptide. Representative cell lines include mammalian cells lines, insect cells, yeast and bacterial cells.

Another object of the invention is to raise antibodies specific to certain domains of the A chain. These antibodies can then be used to block cell adhesion, migration, growth, and neurite outgrowth. The antibodies are raised against the synthetic peptides deduced from DNA sequence and against fusion proteins containing a segment of the A chain produced by bacteria.

A still further object of the invention is a bioengineered laminin A chain expressed by appropriate cells. The genetic engineering technique allows alteration of the DNA sequence resulting in a change of the activity of the A chain. These mutations include a site specific mutagenesis, deletions, insertions and truncations.

An additional object of the invention provides synthetic peptides from the A chain which have biological activity including promoting cell attachment, growth, migration, differentiation and regulating metastasis of tumor cells. One of the peptides possesses the ability to promote neurite outgrowth. Laminin is a very potent and rapid stimulator of neurite outgrowth and promotes both central and peripheral nerve regeneration. Because laminin is a large and antigenic molecule, clinical use of the whole protein may not be feasible. Small synthetic peptides which contain this activity will be very useful and have important clinical applications. The peptide elevates cellular collagenase, an enzyme required to degrade basement membranes which is used by tumor cells to invade tissues and spread, but also by certain normal cells. It also more than doubles the numbers of in vivo tumors formed in mice presumably by elevation of this enzyme. Such activity is important because it provides a direct mechanism by which cells become more malignant and therapies aimed at blocking this activity and/or receptor will presumably reverse the metastatic phenotype. Lastly, such peptides have anti-angiogenic (i.e. inhibit blood vessel formation) activity. This activity could be clinically useful in various diseases where it is not desirable to have an increased blood supply such as hypervascularization in the eye (e.g. a cause of blindness), Kaposi sarcoma lesions, and tumor angiogenesis. Other possible activity and uses of the peptides are being investigated, including their role in cell growth, phagocytosis, and cell migration. These are some examples of possible uses but they point out the wide activities and potential applications of this peptide.

Another object of the invention provides a large quantity production of the A chain and/or a segment of the A chain containing biological activity by expressing the cDNA or genomic clone in appropriate cells.

Another object of the invention provides modifications of synthetic peptides which enhance their activity such as in cell attachment and migration.

A still further object of the invention provides pharmaceutical compositions containing a therapeutically effective amount of one or more synthetic peptides of the A chain. These compositions may further include therapeutically useful agents.

BRIEF DESCRIPTION OF THE DRAWINGS

FIGS. 4.1-4.13 show the nucleotide sequence and deduced amino acid sequence from the laminin A chain cDNA;

FIG. 5 shows the alignment of repeating sequences in domain G;

Figure 6:
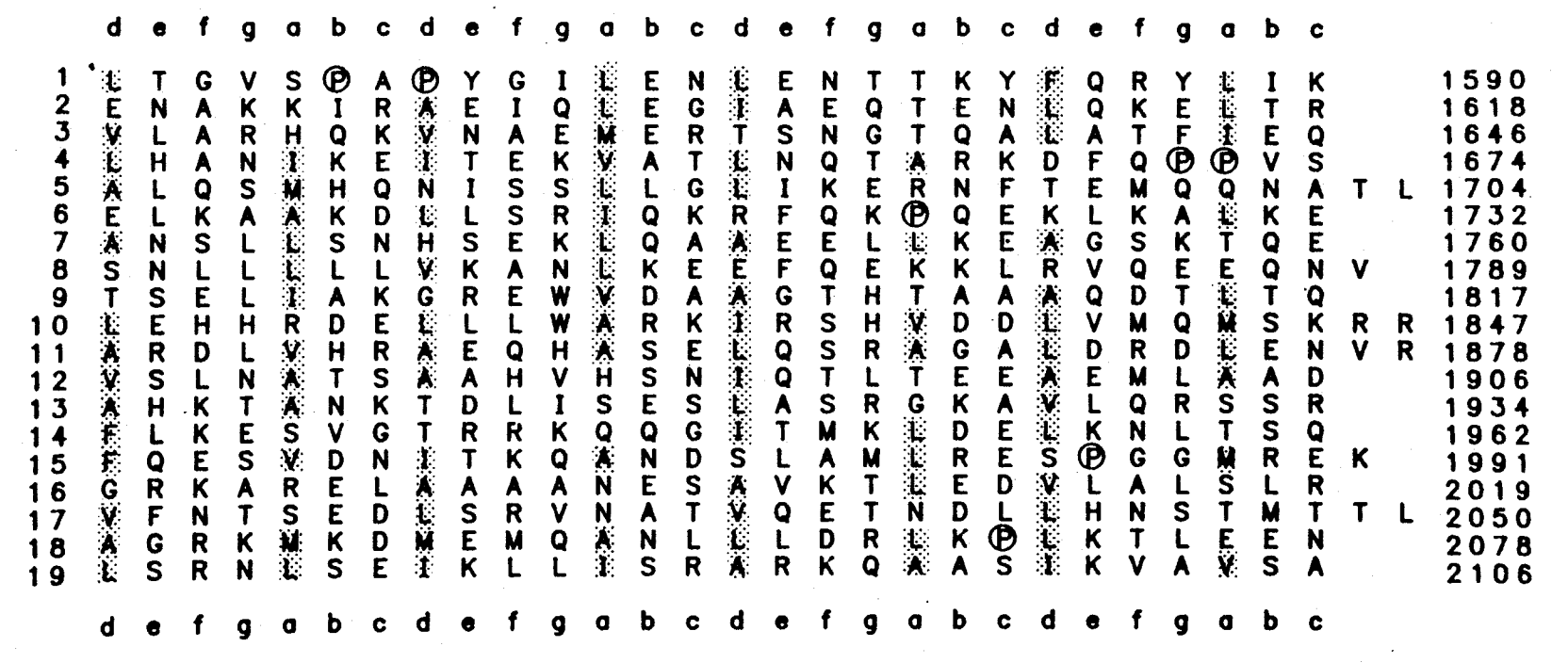

FIG. 6 shows the heptad repeat in domains I and II of the A chain;

FIG. 7 shows the alignment of cysteine-rich repeats in domains IIIa, IIIb, and V of the A chain;

FIG. 8 shows the homology in domains IVa and IVb of the A chain and domain IV of the B2 chain;

FIG. 9 shows the homology of domain VI in the A, B1, and B2 chains;

FIGS. 17A-B show the effect of peptide PA22-2 on promoting PC12 process formation relative to laminin;

FIGS. 18A-C show the effect of synthetic peptide on human umbilical vein endothelial cell adhesion and tube formation;

FIG. 25 shows the effect of antibody to synthetic peptide 10A from the A chain of laminin on inhibiting laminin-mediated neurite outgrowth.

DETAILED DESCRIPTION OF THE INVENTION

Figure 1:
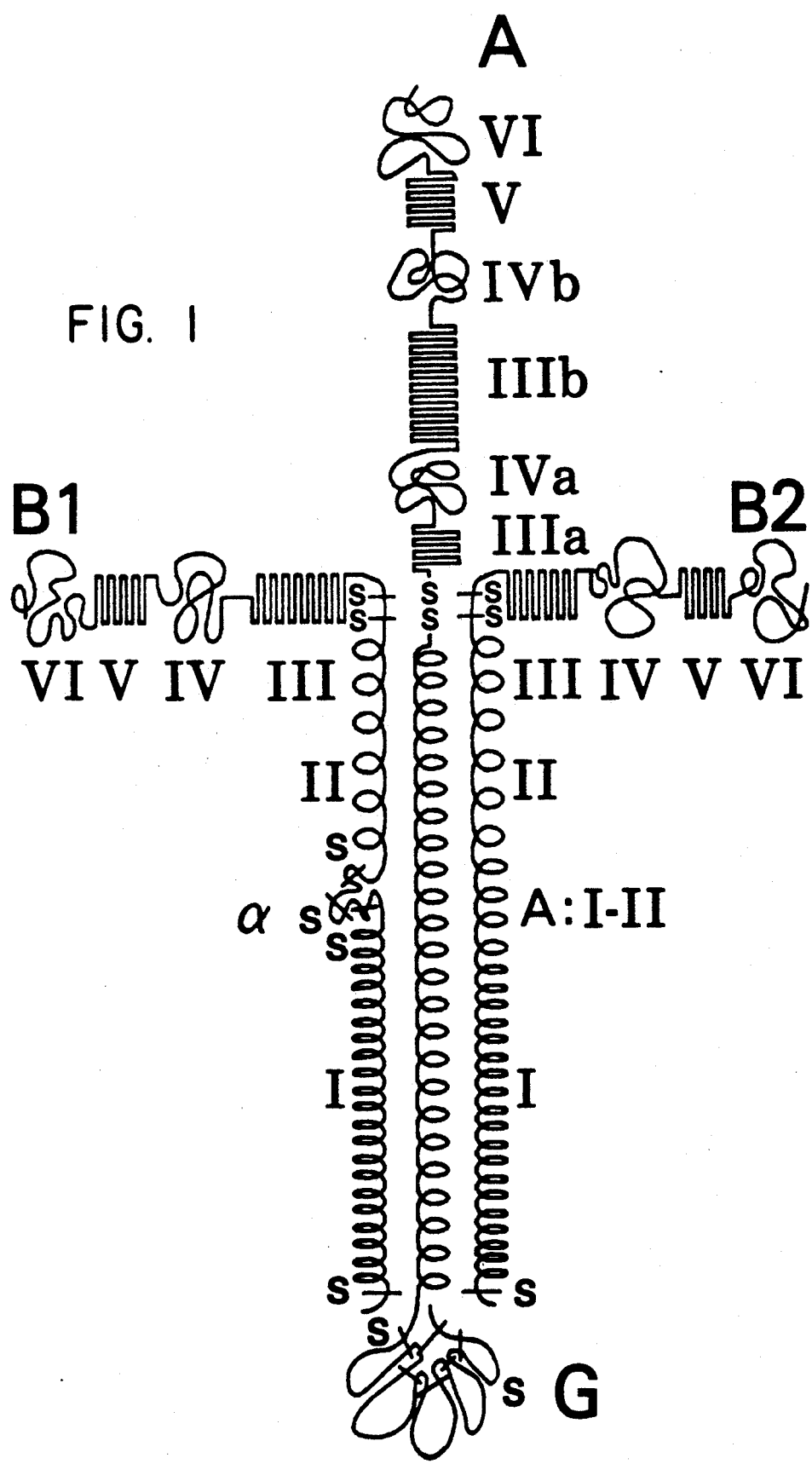
FIG. 1 shows a structural model of laminin.

The above and various other objects of the present invention are accomplished by utilizing cDNA clones coding for the A chain of laminin (see FIG. 3) and a method for producing synthetic peptides and a fragment of the A chain.

Laminin ($M_r = 800,000$) is a glycoprotein consisting of three chains, A, B1, and B2 and has diverse biological activities. Previously, we reported the complete primary structure of the B1 and B2 chains of mouse laminin deduced from cDNA sequence (Sasaki et al, (1987) *Proc. Natl. Acad. Sci.* U.S.A. 84, 935-939; Sasaki and Yamada, (1988) *J. Biol. Chem.* 262, 17111-17117). Here, we describe the isolation, characterization, and sequence of cDNA clones spanning 9520 bases which encode the entire A chain of mouse laminin. The nucleotide sequence of the clones contains an open reading frame of 3084 amino acids including 24 amino acids of a signal peptide. The A chain contains some eight distinct domains including α-helices, cysteine-rich repeats and globules. There is considerable sequence and structural homology between the A chain and the B1 and B2 chains. However, the A chain has a unique globular structure containing homologous repeats at the carboxyl terminus and constituting one third of the molecular mass of the chain. Further, the A chain contains three globules and three cysteine-rich domains at the amino terminus whereas the B1 and B2 chains have only two each of such domains. The A chain shows homology to the basement membrane heparan proteoglycan core and the extracellular domain of the Drosophila neurogenic protein, Notch. There is a RGD sequence in one of the cysteine-rich domains of the A chain. This potential cell binding sequence could be active as another adhesion signal in addition to the previously identified cell binding sequence, YIGSR, of the B1 chain.

Laminin, a glycoprotein localized specifically in basement membranes, is a potent regulator of epithelial cell behavior. Numerous studies indicate that laminin has diverse biological activities which include stimulating adhesion, migration, growth, and differentiation of various cells (Kleinman, et al (1985) *J. Cell Biochem.* 217, 317-325; Martin et al (1987) *Ann. Rev. Cell Biol.* 3, 57-85). Laminin also induces neurite outgrowth (Baron van Evercooren et al (1982) *J. Neurosci. Res.* 8, 179-194) and increases the metastatic ability of tumor cells (Terranova, V. P. et al (1984) *Science* 226, 982-985). It binds cells through cell surface receptors and interacts with other components of basement membranes including collagen IV, heparan sulfate proteoglycan and nidogen/entactin.

Laminin is composed of three chains, B1 (Mr=222,000), B2 (Mr=210,000), and A (Mr=400,000) which are joined by disulfide bonds into a cross-shaped molecule comprising one long and three short arms with globules at each end (Cooper, A. R., et al (1981), *Eur. J. Biochem.* 119, 189-197; Engel, J., et al (1981), *J. Mol. Biol.* 150, 97-120). Studies with proteolytic fragments, domain-specific antibodies and synthetic peptides have identified different regions of laminin with biological activity. A major cell binding site was initially identified on the proteolytic fragments, which encompass the portion of the molecule where the three short arms intersect (Terranova, V. P., et al (1983), *Proc. Natl. Acad. Sci.* USA. 80, 444-448). Subsequently, a pentapeptide, YIGSR (Tyr-Ile-Gly-Ser-Arg) from the cysteine- rich domain of the B1 chain was found to be active for cell attachment, receptor binding, and chemotaxis and was able to prevent the metastasis of tumor cells in experimental animals (Graf. J., et al (1987), *Cell* 48, 989-996; Iwamoto, Y., et al (1987), *Science* 238, 1132-1134; Iwamoto, Y., et al (1988), *J. Cell Physiol,* 134, 287-291). Recently, a fargment from the carboxyl half of the long arm of laminin has been shown to have a high affinity cell-binding site (Aumailley, M. et al (1987), *J. Biol. Chem.* 262, 11532-11538; Goodman, S. L. et al (1987), *J. Cell Biol.* 105, 589-598). This region has also been shown to promote neurite outgrowth by various neuronal cells (Edgar, D., et al (1984), *EMBO J.* 3, 1463-1468; Engvall, E., et al (1986), *J. Cell Biol.* 103, 2457-2465). Heparin binds to the globule at the end of the long arm as well as to the short arms of laminin (Sakashita, S., et al (1980), *FEBS Lett.* 116, 243-246; Skubitz, A. B., et al (1988), *J. Biol. Chem.* 263, 4861-4868). Collagen IV binding sites have been assigned to the terminal regions of the short and long arms (Rao, C. N., et al (1982), *J. Biol. Chem.* 257, 9740-9744; Charonis, A. S., et al (1986), *J. Cell Biol.* 103, 1689-1697; Laurie, G. W., et al (1986), *J. Mol. Biol.* 189, 205-216).

The complete primary structure of the B1 and B2 chains of both mouse (Barlow, D. P., et al (1984), *EMBO J.* 3, 2355-2362: Sasaki, M., et al (1987), *Proc. Natl. Acad. Sci.* USA 84, 935-939; Sasaki, M. et al (1987b), *J. Biol. Chem.* 262, 17111-17117) and human laminin (Pikkarainen, T., et al (1987), *J. Biol. Chem.* 262, 10454-10462; Pikkarainen, T., et al (1988), *J. Biol. Chem.* 263, 6751-6758) as well as of the B1 chain of Drosophila laminin (Montell, D. J., et al (1988), *Cell* 53, 463-473) have been deduced from cDNA sequencing. These results indicate that the B1 and B2 chains have similar structural features with some six different domains. The carboxyl terminal portions of the B chains are rich in α-helix and presumably form a double or triple coiled-coil structure in the rod-like portion of the long arm. Each short arm is formed by the N-terminal portion of one of the chains. In this region, the B1 and B2 chains have two globules separated by two cysteine-rich rod-like domains which consist of many homologous repeats each containing 8 cysteines and approximately 50 amino acids.

Here, we report cDNA clones coding for the entire A chain of mouse laminin. The deduced amino acid sequence reveals that the A chain is also a multi domain protein containing many structural features in common with the B1 and B2 chains. The A chain, however, has a large globular structure at the carboxyl terminus which is distinct from the B1 and B2 chains.

The methodology for construction and isolation of the cDNA clones of the present invention is described in detail in Example 1 below.

EXAMPLE 1

A. Peptide purification and sequencing

Laminin from EHS tumors was reduced with dithiothreitol at 37° C. with sodium iodoacetate following standard procedures (Timpl, R., (1979), *J. Biol. Chem.* 254, 9933-9937). The polypeptide chains were separated on a 3.5% SDS gel (5 mm thick, 200 mm wide), typically loading 20-40 mg. Protein bands were visualized by soaking the gel in 4M sodium acetate for 15 minutes. The 400KD band of the A chain was excised and electroeluted. After dialysis against 0.4M sodium acetate, the isolated polypeptide chain was precipitated by the addition of 9 volumes of ethanol. For cleavage with trypsin, the A chain dissolved in 0.2M sodium bicarbonate was incubated overnight at 37° C. with an enzyme to substrate ratio of 1:30. Molecular sieve column chromatography was done on two tandemly arranged TSK 2000SW columns (1×60 cm, Toyo Soda Tokyo, supplied by Beckman), using a volatile 0.2M ammonium acetate buffer containing 0.1% trifluoroacetic acid (TFA). For reversed phase separations, Vydac C18 columns (201TP54, Separations Group) were used at 55° C. with gradients of 0.1% TFA (solvent A) against 70% acetonitrile in 0.1% TFA (solvent B). Amino acid sequences were determined with 0.1-2 nmol samples on a gas phase (model C70A, Applied Biosystems) or a spinning cup liquid phase sequencer (model 890, Beckman). The gas phase sequencer was equipped with an on-line PTH amino acid analysis system built from a HPLC micro pump (model G, Brownlee Labs) and a spectroflow 773-UV detector (Kratos). The separation of PTH derivatives was carried out by gradient elution on a PTH C-18 microbore column (2.1×220 mm, Applied Biosystems) following the manufacturer's instructions. PTH amino acids from the spinning cup sequencer were identified on a supershere RP-8 column (4×250 mm, Merck) using an isocratic HPLC system.

B. Construction and screening of cDNA libraries

Three different types of cDNA libraries in a λgtll vector were constructed from two RNA sources. Poly(A)+ RNA prepared from the Engelbreth-Holm-Swarm (EHS) tumor was fractionated on a sucrose density gradient and fractions larger than 28S were pooled as described in (Sasaki, M. et al (1987b), *J. Biol. Chem.* 262, 17111-17117), which is herein incorporated by reference. Differentiated F9 cell poly(A)+ RNA was prepared from F9 cells after treatment with retinoic acid and dibutyryl cAMP for 5 days (Sasaki, M., et al (1987a), *Proc. Natl. Acad. Sci.* USA 84, 935-939) and used as a template without size fractionation. Oligo dT-primed cDNA synthesis was carried out as described in Sasaki, M. et al (1987b), *J. Biol. Chem.* 262, 17111-17117. Double stranded cDNA was blunt-ended with T4 DNA polymerase, treated with EcoR1 methylase, ligated to EcoR1 linkers, and the linkers were digested with EcoR1 (Sasaki, M., et al (1987a), *Proc. Natl. Acad. Sci.* USA 84, 935-939).

The cDNA was size fractionated by 1% agarose gel electrophoresis, and fractions larger than 1 kb were used to ligate into EcoR1 cut λgtll DNA (Vector Cloning System). Three different specific primed cDNA libraries were constructed from differentiated F9 cell poly(A)+ RNA as described in Sasaki, M. et al (1987b), *J. Biol. Chem.* 262, 17111-17117. These oligonucleotides were 5' dCTGCCCTGTGGACCAGGTCACGGGC, 5'-dCTCGACAGCTTTCCGGCCAACCTCC and 5'-dGGTCACTGTCCACCGTCTCCACTGG, which are complementary to the sequences at nucleotide positions from 5,662 to 5,686, from 4,089 to 4,113, and from 1,885 to 1,879 as underlined in FIG. 4.

Figure 3:
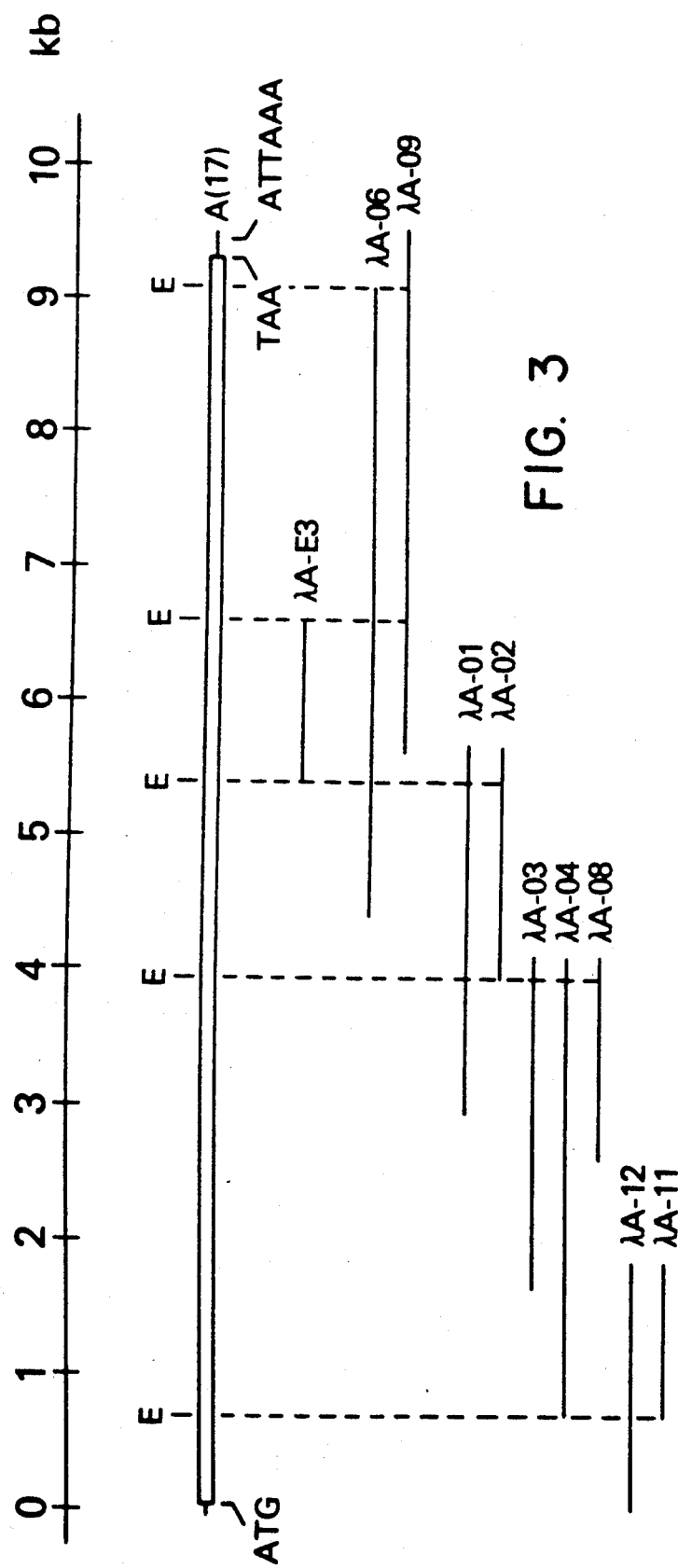
FIG. 3 shows the overlapping of cDNA clones for the A chain of laminin.

The EHS cDNA library was screened with antibodies to denatured laminin as described (Sasaki, M. et al (1987b), *J. Biol. Chem.* 262, 17111-17117). The oligo dT primed F9 cDNA library was screened with a 32p labeled cDNA insert from A-E3 (see FIG. 3). FIG. 3 shows overlapping cDNA clones for the A chain of laminin. The lines indicate the size and order of the clones. E indicates internal EcoR1 sites. The specific oligonucleotide cDNA libraries were screened with $^{32}$p-labeled probes from the most 5' portion of the previous cDNA clones in each screening step.

FIG. 4 shows the nucleotide sequence and deduced amino acid sequence from the laminin A chain cDNA. The contiguous cDNA sequence determined from the overlapping clones is shown. The predicted amino acid is shown below the cDNA sequence beginning at nucleotide 49. The 46 potential glycosylation sites (NXT or NXS) are double underlined. There are 163 cysteines (circled). The calculated molecular weight of the mature protein is 335,729 daltons. Oligonucleotides used for primer extension are underlined The asterisk indicates a termination codon.

C. DNA sequence and analysis

The DNA sequence was determined by the dideoxy-chain termination method of Sanger et al (Sanger, F., et al (1980), *J. Mol. Biol.* 143, 161-178), which is herein incorporated by reference, and with a "shotgun" random fragment strategy. Direct sequencing of the DNA in λgtll was performed using forward and reverse primers as described by the supplier (New England Biolabs). The nucleotide sequences were analyzed by the programs of Staden (Staden, R. (1982), *Nucleic Acids Res.* 10, 2951-2961), IDEAS (Kanehisa, M. (1984), *Nucleic Acids Res.* 11, 417-428), and the Protein Sequence Query (PSQ, Protein Identification Resource, National Biomedical Research Foundation). Internal homology of the A chain and homology to the B1 and B2 chains were analyzed by DOTMATRIX (PSQ), SEQHP and SEQDP (IDEAS). FASTA developed by Pearson and Lipman (Pearson, W. R., et al (1988), *Proc. Natl. Acad. Sci.* USA 85, 2444-2448 ) was used for the homology search of the National Biomedical Research Foundation (NBRF) protein data base. The protein structure was analyzed by DELPHI, ALOM, CHOFAS, and HPLOT of IDEAS.

D. Results

Figure 2:
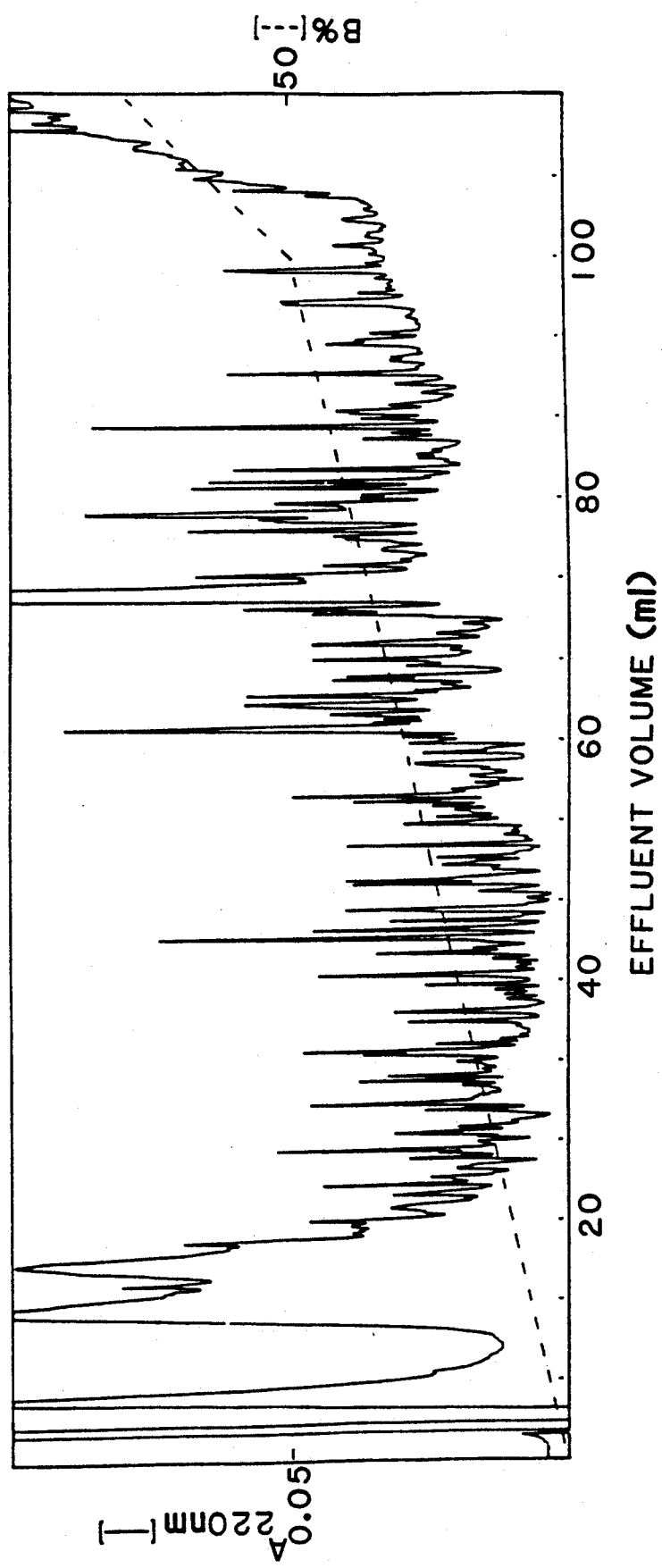
FIG. 2 shows the separation of tryptic peptides of the A Chain.

1. Isolation and sequencing of peptides from the A chain of laminin Laminin prepared from EHS tumor was reduced and subjected to preparative slab gel electrophoresis. The A chain protein (Mr-400 KD) was excised, extracted and subjected to proteolysis. FIG. 2 shows the separation of a tryptic digest of the A chain. For preparative isolation of peptides, the A chain was first cleaved with the lysine specific protease, endoproteinase Lys-C, and the resulting fragments were partially separated by reversed phase chromatography on a Vydac C18 column. More specifically, the tryptic digest of the laminin A chain was separated by reverse phase chromatograph on a Vydac C18 column in 0.1% trifluoroacetic acid with a linear acetonitrile gradient The collected pools were then further digested with trypsin and separated by molecular sieve and reverse phase chromatography. Although a large number of peptides were obtained, only 18 have been sequenced as shown below in Table I.

TABLE I

| Aminoterminal amino acid sequences of tryptic peptides from the A-chain. | | |
|---|---|---|
| Sequences of trytic peptides | Length | Residues |
| T1: AYQPQTSSTNYNTLI | 15 | 2,113-2,129 |
| T2: ADNEVICT(S)YYSK | 13 | 158-171 |
| T3: YTVSYDIPVETV | 12 | 572-583 |
| T4: AEGLSLQPYEEYFNVVR | 17 | 606-624 |
| T5: EASAAENPPVRTSK | 14 | 2,203-2,218 |

TABLE I-continued

Aminoterminal amino acid sequences of tryptic peptides from the A-chain.

| Sequences of tryptic peptides | Length | Residues |
|---|---|---|
| T6: DLIYVGGLPHSK | 12 | 2,416–2,429 |
| T7: NSYGVR | 6 | 2,457–2,464 |
| T8: QHIYAEYPFWR<br>  PFY | 11 | 1,193–1,205 |
| T9: YTVSYDIPVETVDSDLMXHAD(IEMK) | 22 | 572–595 |
| T10: (L)TATYYWAAP(E)AYLGNK<br>  S | 17 | 546–564 |
| T11: TIDISNLYIGGLPEDK | 16 | 2,600–2,617 |
| T12: CSAGYHGNPR | 10 | 1,474–1,485 |
| T13: AESPHTHSTSADTNDPIYVGGYPAHVK<br>  I | 27 | 2,985–3,013 |
| T14: QGLLAVFDAYDTSDK | 14 | 2,382–2,397 |
| T15: TQEPDNLLFYLGSSSSSDFLAVE | 23 | 2,132–2,156 |
| T16: YFNSVSEK | 8 | 1,279–1,288 |
| T17: AFMTVDGQESPSVTVVGNATTLDVER | 26 | 2,794–2,821 |
| T18: TLEDVLALXLR | 11 | 2,009–2,02 |

Residues in parentheses indicate uncertain acids. Letters underneath the peptide sequences represent residues from cDNA which differ from the protein sequence.

As described below, the occurrences of these peptides in the cDNA sequence allowed the definitive identification of A chain cDNA clones.

2. Isolation and characterization of overlapping cDNA clones.

Three different types of cDNA libraries were screened to obtain a series of overlapping clones coding for the entire A chain of mouse laminin (see FIG. 3). Initially an oligo (dT)-primed cDNA library from EHS tumor cell poly (A)+ RNA was prepared in a λgt11 expression vector and was screened with polyclonal antibody to denatured laminin. A dozen clones out of several hundred positives were picked randomly and purified. These clones were characterized first by Northern analysis to RNA prepared from teratocarcinoma F9 cells grown under standard conditions (Maniatis et al (1982) *Molecular Cloning: A Laboratory Manual* Cold Spring Harbor Lab., Cold Spring, N.Y.) following treatment with retinoic acid and dibutyryl cAMP which induces a 20-fold increase in the synthesis of laminin and collagen IV. All clones hybridized strongly to RNA from differentiated F9 cells but not from undifferentiated F9 cells. Northern analysis indicated that there were three different classes of cDNA. Class I and II clones hybridized to 6.5 and 8.0 kb RNA transcripts, respectively. The third group hybridized to a mRNA transcript of 10 kb. DNA sequence analysis revealed that the class I and II clones coded for the B1 and B2 chains. The amino acid sequence deduced from one of the class III clones (λA-E3) matched the partial amino acid sequence of the proteolytic peptide, T15 (see Table I above) of the mouse A chain, as described above. This clone was subsequently used as a probe to screen a newly prepared oligo (dT)-primed cDNA from differentiated F9 cell poly(A)+ RNA. Twelve positive clones were purified and characterized including λA-06 and λA-09 (see FIG. 3).

The remaining sequence of the A chain was obtained by isolating overlapping cDNA clones from libraries constructed by specific primer extension. Oligonucleotides 25 bases long were synthesized complementary to the 5' region of each successive clone and were used as primers to prepare new cDNA libraries from differentiated F9 cell poly(A)+ RNA. The libraries were screened by plaque hybridization using a restriction fragment of the 5' portion of the previous clone. Lambda A−01, −02, −03, 04, −08, −11 and −12 are representative of multiple isolates obtained at each successive cloning step (see FIG. 3).

The clones were first examined by sequencing both ends and then their authenticity was checked by S1-protection analysis. Using these approaches, we obtained a series of overlapping clones which extend over 9.5 kb of contiguous DNA. Primer extension analysis revealed that the most 5' clone, λA-12 was missing 80 nucleotides at the 5' end of mRNA. The largest clones obtained at each screening step were sequenced by the random fragment method.

3. Multi-domain structure of the A chain cDNA sequence—The complete 9520 bp sequence of the A chain cDNA and deduced amino acid sequence were determined (see FIG. 4). There is an open reading frame of 3084 amino acids starting with a methionine followed by a stretch of 24 mostly hydrophobic amino acids whose sequence is characteristic of signal peptide. Although the amino terminal sequence of the A chain is not known, a signal peptidase cleavage site was presumed according to the "−3, −1" rule by von Heijne (von Heijne, G. (1986), *Nucleic Acids Res.* 10, 183–196) and the most amino terminal residue, glutamine was numbered +1. Following the large open reading frame, there is about 200 bp of a 3' untranslated region which contains a polyadenylation signal ATTAAA followed by the poly A sequence. The A chain contains 163 cysteines and 46 N-X-T and N-X-S sequences as potential N-linked oligosaccharide attachment sites.

Analysis of the deduced amino acid sequence suggests that the A chain contains some eight structural domains which show sequence homology to the B1 and B2 chains. The A chain, however, has an additional carboxyl terminal domain which is largely globular. The domain structure of the A chain together with those of the B chains is schematically illustrated in FIG. 1. In the structural model of laminin illustrated in FIG. 1, the Roman numerals designate the general regions of the domains in each chain. Thus, the A chain domains are numbered according to the format used previously for the B1 and B2 chains and the large carboxyl terminal domain is designated G.

Figure 5:
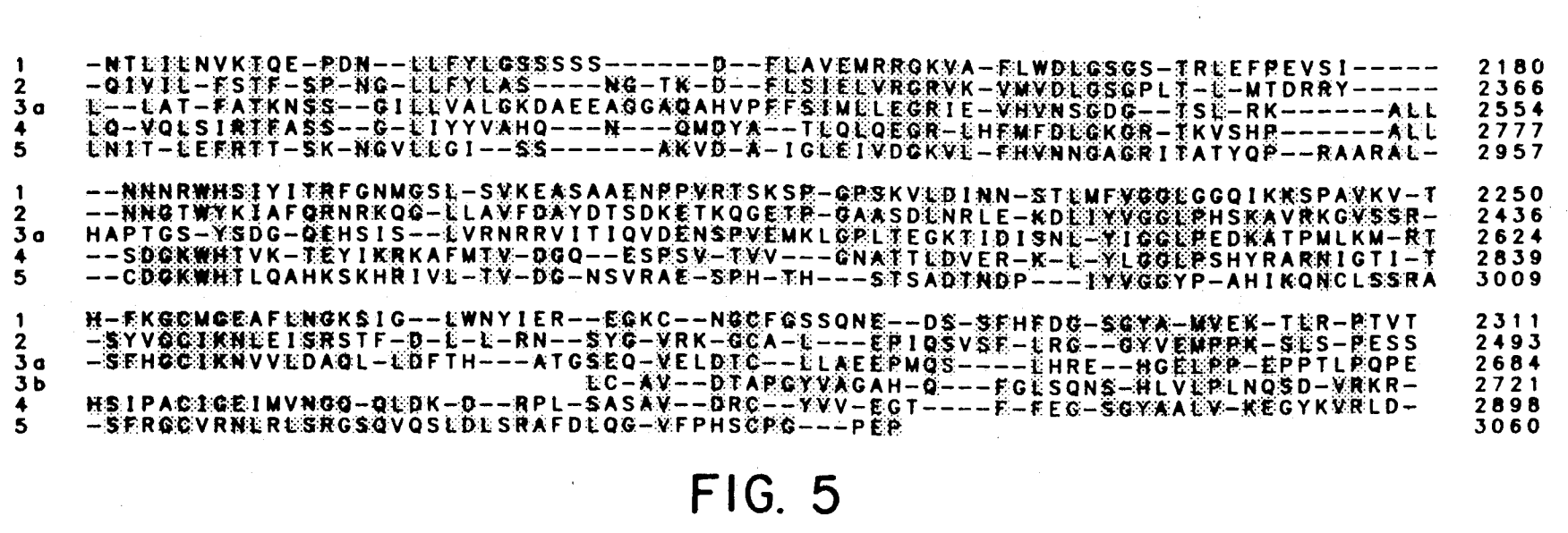

The carboxyl terminal globular domain—Domain G (residues 2,110–3,060) has 951 amino acids (Mr=103,986). Computer assisted structural analysis suggests that the domain forms a globular structure agreeing with the image of the rotary-shadowed laminin observed in the electron microscope. Computer analysis by the program SEQHP indicates that domain G has an internal repeating structure made up of 5 tandem repeats (see FIG. 5). Thus, FIG. 5 shows the alignment of repeating sequences in domain G. Residues 2,124 to 3,054 of domain G which comprises five repeats containing approximately 180 amino acids each are shown in an alignment derived using the program SEQHP. Some gaps were introduced after visual inspection. The numbers at the right end in each line represent residue numbers. Residues are shaded when a majority of the residues are conserved in equivalent positions. Each repeat contains glycines at regular intervals, in which 25 out of 86 glycines are completely conserved. The location of hydrophobic and charged residues are also highly conserved.

There are 15 cysteines in the domain of which ten are aligned at the same positions in the repeat. Analysis with the computer program ALOM indicated a potential transmembrane segment at residues 2,313 to 2,329.

α-helical domains—Domains I and II (residues 1,538-2,109) have 571 amino acids (Mr=64,025) and are predominantly α-helical. Both domains have almost the same structural feature, but were numbered I and II so that the relative positioning of domains is consistent among the three chains. Similar to the corresponding domains of the B1 and B2 chains, domains I and II of the A chain contain a series of heptad repeats in which hydrophobic amino acids are located at regular intervals as shown in FIG. 6. The sequence (residues 1,563 to 2,106) of domains I and II of the A chain are aligned so that hydrophobic residues (shaded) occur predominantly in positions a and d and form a hydrophobic interaction edge. The heptad repeats are characteristic of proteins containing coiled-coil structure such as fibrinogen (Doolittle, R. F., et al (1978), *J. Mol. Biol.* 120, 311-325) and myosin (Mclachlan A. D., et al (1983), *J. Mol. Biol.* 15, 605-625). The size of domains I and II of the A chain is very similar to those in the B1 and B2 chains. The domains of the A chain, however, lack the cluster of polar amino acids present in domain I of the B1 and B2 chains. The A chain also contains seven prolines which could interrupt the α-helix.

Figure 7:
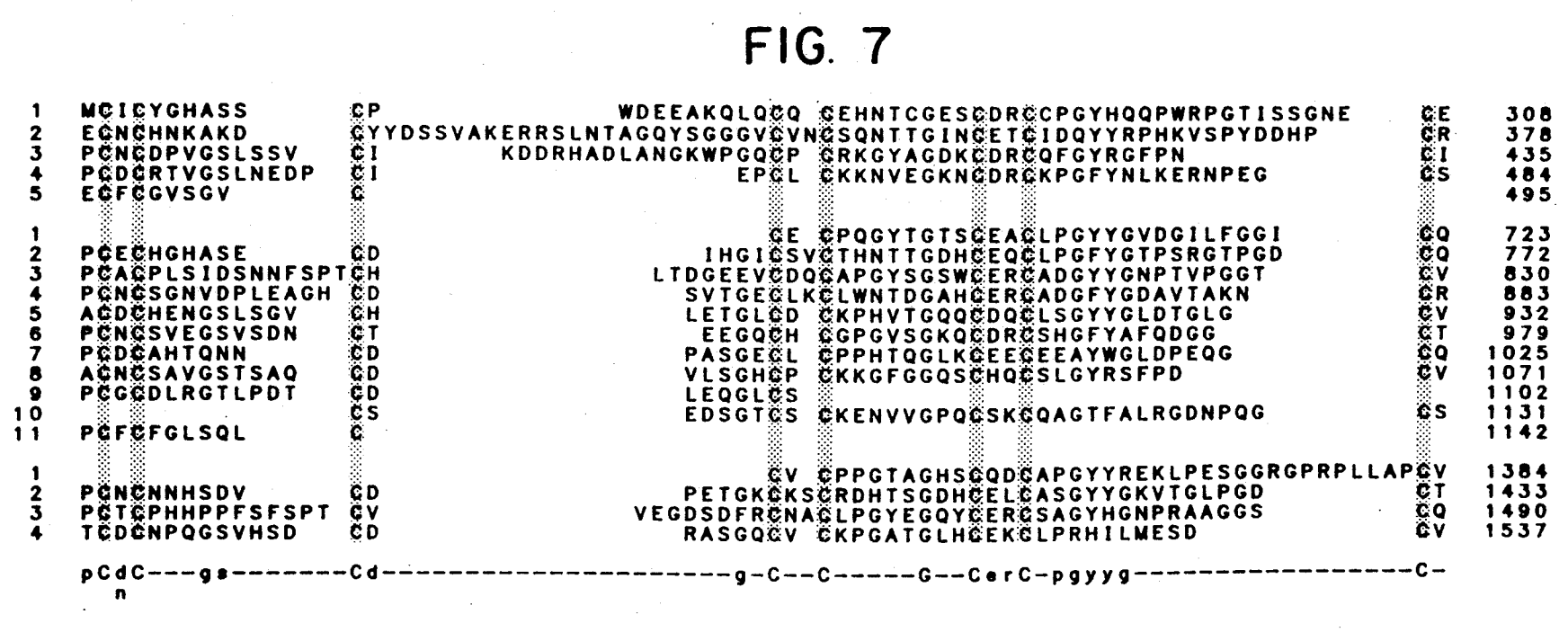

Cysteine-rich domains—Domains IIIa (Mr=20,329, residues 1,345-1,537), IIIb (Mr=47,091, residues 692-1,142), and V (Mr=27,020, residues 252-495) are rich in cysteines and glycines which create many turns and contain many homologous repeats. FIG. 7 shows the alignment of cysteine-rich repeats in domains IIIa, IIIb, and V of the A chain. The sequences, including residues 251-495 in domain V, residues 692-1,142 in domain IIIb, and residues 1,345-1,537 in domain IIIa, are aligned by the program SEQHP, with some gaps introduced by visual inspection. Cysteines are shaded. The numbers at the right end in each line represent residue numbers. A consensus sequence is shown on the bottom line. Each homologous repeat is composed of a 50 amino acid-unit with 8 cysteines. The distance between the first, second and eighth cysteines, and between the fifth, sixth and seventh cysteines is completely conserved. These repeats are the same type as found in the corresponding domains III and V of the B1 and B2 chains. Domain IIIb at 1,123-1,125 contains an RGD sequence which is a potential cell attachment site. Twenty-two out of about fifty amino acid positions are highly conserved, which allows the abovementioned consensus sequence to be deduced (see FIG. 7).

Amino terminal globular domains—Domains IVa (Mr=22,742, residues 1,143-1,344), IVb (Mr=21,968, residues 496-691), and VI (Mr=28,695, residues 1-251) contain mixtures of α-helix, β-sheet, and random coil and are likely to form globules which are clearly evident in electron micrographs of laminin. There is a significant homology (about 25% identity) between IVa and IVb and between these domains and domain IV of the B2 chain. FIG. 8 shows homology in domains IVa and IVb of the A chain and domain IV of the B2 chain. The sequence of residues 513 to 687 of domain IVa of the A chain, residues 1,161 to 1,339 of domain IVb of the A chain, and residues 511 to 650 of domain IV of the B2 chains are aligned by the program SEQHP. Conserved residues are shaded.

Domain VI does not share sequence homology to domains IVa and IVb. There are no cysteines in domains IVa and IVb whereas the most amino terminal domain, domain VI, contains 15 cysteines. Domain VI of the A chain is highly homologous to domain VI of the B1 and B2 chains and an alignment of these sequences is shown in FIG. 9. Sequences of residues 1 to 251 of the A chain, residues 1 to 248 of the B1 chain, and residues 1 to 249 of the B2 chain are aligned by the program of SEQHP. Conserved amino acids are shaded.

4. Sequence homology in the three chains

Figure 10:
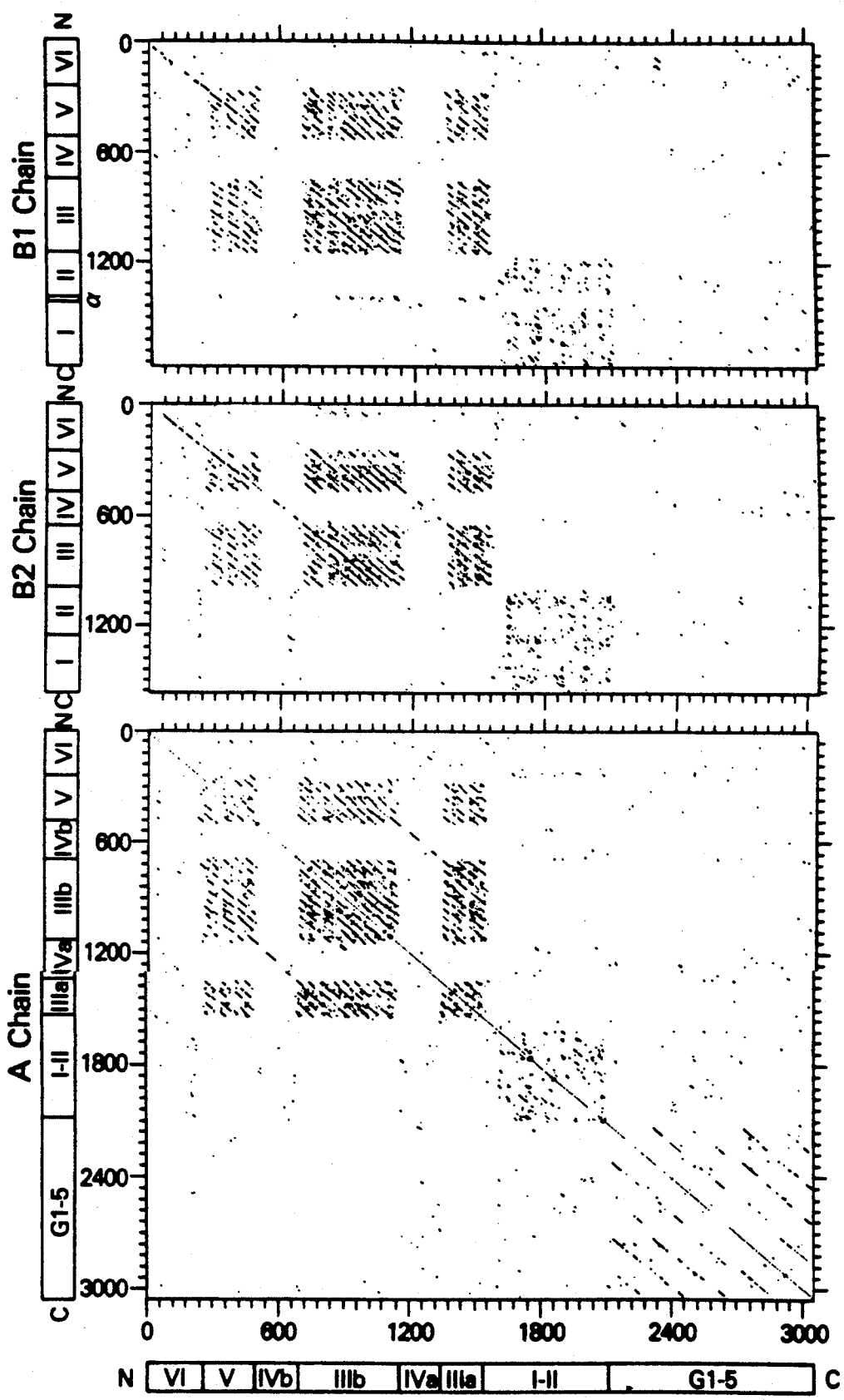
FIG. 10 shows a dot-matrix analysis of the amino acid sequence of the laminin chains.

Sequence homology between the A chain and the B chains and within the A chain was analyzed by the Dot-Matrix program as illustrated in FIG. 10. The sequence homology was analyzed by the program DOT-MATRIX (PSQ) with a window length of 25 and a score of 25 or greater. Points at which the two sequences are homologous are indicated by dots. At the top, the amino acid sequence of the A chain is compared to that of the B1 chain. In the center, the amino acid sequence of the A chain is compared to that of the B2 chain. At the bottom, the amino acid sequence of the A chain is compared to itself. The internal homologies of the A chain shown by diagonal lines are apparent. Domain G contains 5 relatively large repeats and is unique to the A chain. The α-helical domains I and II show numerous short homologies because of the heptad repeat. The cysteine-rich domains, IIIa, IIIb, and V, show homologous sequences within the domains as well as between them, and are very similar to domains III and V of the B1 and B2 chains. The globular domains IVa and IVb are homologous to each other and to domain IV of the B2 chain but not to that of the B1 chain. The sequence of the terminal domain VI is also significantly conserved in all three chains.

E. Discussion

Laminin is one of the key extracellular matrix components which influence tissue development and function. As one might expect from an extraordinary large and complex molecule, different portions of laminin have been shown to be active in various biological functions. Together with the previously determined sequence of the B1 and B2 chains, the primary structure of the A chain described hereinabove allows for the first time one to predict the alignment of the three chains, as well as to provide insight into the detailed structure of the molecule.

The amino two-thirds of the A chain has a significant sequence homology to that of the B1 and B2 chains. There are, however, some structural differences between this region of the A and the B chains. Whereas the B1 and B2 chains have only two globules and two cysteine-rich domains, this portion of the A chain has three globules, domain IVa, IVb and VI which are separated by three cysteine-rich domains: IIIa, IIIb and V. This is in contrast to electron microscopic observations on laminin which revealed only two globular domains in each short arm. One possible explanation could be that the third globule is in a near central position and might therefore have been overlooked. The A chain globules, domain IVa and IVb, are homologous to each other and are also homologous to domain IV of the B2 chain. The region encompassing domains IIIa to IVb of the A chain is likely to have evolved by duplication of a sequence containing a globule fused to a rod structure. The most amino terminal globule, domain VI of the A chain, has a significant sequence homology with the B1 and B2 chains (about 30% identity) as shown in FIG. 9 but is distinctive from the other globular domains. The high degree of sequence conservation of this domain in the three chains suggests a common function Indeed, the ends of short arm have been thought to be involved in collagen IV binding (Rao, C. N., et al (1982), *J. Biol. Chem.* 257, 9740–9744).

The α-helical domains, domains I and II of the three chains, could form a triple-stranded coiled-coil structure since the total number of residues in those domains is almost the same in all chains. These regions likely constitute the rod-like portion of the long arm of the molecule because the length (85 nm) of domains I and II calculated assuming a distance of 0.15 nm per residue in α-helix corresponds well to the electron microscopic measurement (77 nm) of this part of the rotary-shadowed laminin. The heptad repeats in the domain II of the A chain are less periodic than domain I, similar to the B1 and B2 chains. This region of the A chain also contains five prolines which disturb the α-helix. These features suggest that the amino terminal portion of the rod-like region of the long arm forms less rigid interactions between chains compared to the carboxyl terminal part. The interaction between the three chains is likely to be further stabilized by disulfide bonds at both boundaries of the rod-like domain. Two cysteines from domain I of the B1 and B2 chains are involved in the formation of intermolecular disulfide bonds (Paulsson, M., et al (1985), *EMBO J.* 4, 309–316). At the center of the cross, six cysteines, two donated from each chain, could also form disulfide bonds to stabilize the structure. It is of interest to note that there is an interruption in the rod-like region of the long arm by domain α in the B1 chain. Domain α is about 30 residues long and contains 6 cysteines, 8 glycines and 3 prolines which generate many turns (Sasaki, M., et al (1987a), *Proc. Natl. Acad. Sci.* USA 84, 935–939; Pikkarainen, T., et al (1987), *J. Biol. Chem.* 262, 10454–10462). The B2 and A chains do not have a corresponding domain. Domain α might be a site of interaction with other basement membrane proteins, or with other laminin molecules to form dimeric or multimeric proteins.

The A chain sequence data allowed an exact localization of laminin fragment, E8 which has been shown to stimulate neurite outgrowth and cell attachment (Edgar, D., et al (1984), *EMBO J.* 3, 1463–1468; Aumailley, M., et al (1987), *J. Biol Chem.* 262, 11532–11538). Fragment E8 is a 35 nm long rod-like structure with a globule derived from the carboxyl half of the long arm. In agreement with the model for the laminin structure it contains segments of all three chains. Amino terminal sequence analysis (Deutzmann et al., submitted) revealed that fragment E8 contains the 226 and 246 amino acids consisting of carboxyl terminal portion of the B1 and B2 chains, respectively. The A chain starts at position 1,886 (see FIG. 4) and should therefore comprise the terminal 223 amino acids of the λ-helical region, in good agreement with the length of the B chain segments.

The cysteine-rich domains show a strong homology in all three chains. Eight cysteines are positioned at regular intervals and the distances between the cysteines which do not have gaps in the repeats are strictly conserved in all chains. Further, the consensus sequence of the cysteine-rich domains of the A chain is the same as that of the B1 and B2 chains. Glycines as well as cysteines, which generate many turns, are highly conserved suggesting their role in forming a rod-like structure. Interestingly, each cysteine rich domain has a different number of homologous repeats. Such different spacing by these domains may indicate that each short arm has a different functional role.

The carboxyl terminal globule, domain G, comprises one third of the molecular mass of the A chain and has a unique structure different from other regions of the molecule. The globule has been identified as one of the binding sites for collagen IV (Charonis, A. S., et al (1986), *J. Cell Biol.*, 103, 1689–1697), heparin (Ott, V., et al (1982), *Eur. J. Biochem.* 123, 63–72), and basement membrane heparan sulfate proteoglycan (Fujisawa, S., et al (1984), *Eur. J. Biochem.* 143, 145–157). Heparan sulfate protreoglycan binding is thought to be due largely to interactions with basic amino acids because a moderate concentration of salt disrupts its binding. Near the end of the carboxyl terminus, there is a 21 amino acid segment (residues, 3010–3032) which contains 6 positively charged amino acids without interruption by negatively charge amino acids. This segment could participate in heparin binding Computer search of the National Biomedical Research Foundation (NBRF) using the program of FASTA revealed that the cysteine-rich domains of the A chain are homologous to proteins containing epidermal growth factor (EGF)-like repeats such as neurogenic protein Notch in *Drosophila* (Wharton, K. A., et al (1985), *Cell*, 43, 567–581), the lin-12 homeotic protein in soil nematode (Greenwald, I. (1985), *Cell.* 43, 583–590), EGF precursor (Gray, A., et al (1983), *Nature* 303, 722–725), nerve growth factor receptor precursor (Johnson, D., et al (1986), *Cell* 47, 545–554), von willebrand factor precursor (Titani, K., et al (1986), Biochem. 25, 3171–3184), and transforming growth factor (TGF) α(Derynck, R., et al (1984), *Cell* 38, 287–297). The Notch and lin-12 proteins showed much stronger homology with the A chain than the other proteins, with an optimized alignment score of 320 and 250, respectively. Similar homologies to the EGF-like repeat have also been found in the B1 and B2 chains (Sasaki, M., et al (1987a), *Proc. Natl. Acad. Sci.* USA 84, 935–939; Sasaki, M. et al (1987b), *J. Biol. Chem.* 262, 17111-17117; Pikkarainen, T., et al (1987), *J. Biol. Chem.* 262, 10454–10462; Pikkarainen, T., et al (1988), *J. Biol. Chem.* 263, 6751–6758; Montell, D. J., et al (1988), *Cell* 53, 463–473). This homology could reflect some functional relatedness. Recently laminin has been found to exert EGF-like growth factor activity (Engel personal communication). Although the laminin cell binding sequence YIGSR is located in an EGF-homology region of the B1 chain, the pentapeptide does not show EGF-like activity (Carpenter, personal communication). It is conceivable that one of the EGF-like sequences in the B2 and A chains may be responsible for this activity. The Notch locus is involved in cell-cell interaction and is essential for proper differentiation of the ectoderm in Drosophila (Lehman, R., et al (1983), Roux's Arch. Dev. Biol. 192, 62-74). The Notch protein contains 36 EGF-like non-identical repeats at the amino terminal half, each of about 40 amino acids. Analysis of mutations indicate that there are different functions among the EGF-like repeats and that the total number of repeats is important for wild-type Notch protein function (Kelley, M. R., (1987), Cell 51, 539-548). By analogy to these results, it is reasonable to assume that each cysteine-rich domain and each repeat within the domains in the A chain may have a different function. For example, some domains may function as additional cell attachment sites, complementing the cell binding sequence YIGSR contained in the B1 chain.

In contrast to most EGF-like repeats which contain six cysteines in each repeat, the cysteine-rich repeats of the laminin chains exhibit consistently eight cysteines. It is reasonable to assume that the strict conservation of two additional cysteine residues, which are very likely disulfide bonded, is an important feature. They could help stabilize the rod-like structure of the short arms or form loops with yet unknown biological function. In this respect, it is very interesting to note that a portion of the sequence of the basement membrane heparan sulfate proteoglycan core protein (BPG) shows a remarkable structure and sequence similarity to the short arm of the A chain. A partial primary structure of BPG has been determined by cDNA sequencing (Noonan et al, J. Biol. Chem. in press) and shown to contain globules separated by cysteine-rich domains which also contain eight cysteines at similar locations as those in the repeats in the A chain and B-chains of laminin. This might indicate more a wider distribution of this motif. Further, the BPG globules show a significant sequence homology to the corresponding domains of the A chain. Statistical significance of the similarity calculated using SEQDP of the IDEAS' program is shown in Table II.

TABLE II

| | | STATISTICAL ANALYSIS OF DOMAIN IV-LIKE REGIONS | | | |
|---|---|---|---|---|---|
| | | LAM A | | BPG | |
| | | IVa Score (SD) | IVb Score (SD) | G1 Score (SD) | G2 Score (SD) |
| LAM A | IVa | | −192 (14.5) | −211 (20.3) | −232 (20.0) |
| | IVb | −192 (16.2) | | −194 (20.7) | −209 (20.6) |
| LAM B2 | IV | −80 (5.7) | −113 (9.7) | −98 (10.5) | −86 (5.6) |

Table II shows the similarity of domains IVa and IVb of the laminin A chain compared with domain IV of the B2 chain and with globular domains from the basement membrane proteoglycan in a region similar to the short arm regions of the laminin chains. Residue numbers for each domain compared are for the A chain 1143-1344 (IVa) and 496-691 (IVb), for the B2 chain 503-687 (IV) and for BPG5 1-186 (G1) and 394-590 (G2). Analysis was performed using the IDEAS program SEQDP with a gap penalty of 8 and 100 random alignments. The score is determined for the best alignment using the mutation data matrix. This comparison weights individual amino acids and accounts for conservative or radical changes and sums these to give a score. SD is the difference of the optimal alignment score from the scores of 100 random alignments, given in standard deviation units from the mean. Comparisons with domain IV of the laminin B1 chain indicated no similarity of this domain with those above.

The comparison of the two globules, G1 and G2, in BPG with domains IVa and IVb of the A chain reveal a high alignment score (approximately—200) with a difference of 20 standard deviation units from the mean as determined using the mutation data matrix. Similarity between the A chain and BPG is even higher than between domains IVa and IVb of the A chain. Domain IV in the B2 chain shows some similarity to G1 and G2 of BPG whereas domain IV in the B1 chain shows none. The strong conservation of these regions in the A chain and BPG suggest not only evolutionary relatedness but also common biological function between the two. In this context, it is of interest to note that BPG promotes cell binding through a unique cell surface associated protein (Clement et al, in preparation) and that BPG binds to type IV collagen (Hassell, personal communication) similar to the well documented function of laminin.

A pentapeptide, YIGSR from the cysteine repeats in the B1 chain has been identified as being active for cell binding, chemotaxis, and receptor binding (Graf. J., et al (1987), Cell 48, 989-996; Iwamoto, Y., et al (1987), Science 238, 1132-1134). This sequence has not been found in the A and B2 chains. Since the carboxyl terminal portion of long arm has also been shown to be active for cell binding (Aumailley, M., et al (1987), J. Biol. Chem. 262, 11532-11538; Goodman, S. L., et al (1987), J. Cell Biol. 105, 589-598; Edgar, D., et al (1988), J. Cell Biol. 106, 1299-1306) a different sequence must be used for this second site which is capable of interacting with a laminin receptor different from the 67 kd receptor.

It is of interest to note that domain IIIb has an RGD sequence which is know to be a versatile cell binding signal (Ruoslahti, E., et al (1987), Science 238, 491-497). Whether the RGD sequence is functional as a cell binding signal is likely to depend on the surrounding sequences since the RGD sequence is found in many proteins but only a few of them are active as cell attachment sites. It is possible that the RDG sequence in laminin is active for a cell binding since integrin (the fibronectin receptor) can bind to laminin (Horwitz, A., et al (1985), J. Cell Biol. 101, 2134-2144) and an antibody to integrin inhibits interaction of integrin with laminin (Tomaselli, K. J., et al (1986), J. Cell Biol. 103, 2659-2672). Furthermore, it has been shown that endothelial cell attachment to a laminin substrate is inhibited by a RGD-containing synthetic peptide (Tashiro and Grant, personal communication) suggesting that laminin-mediated cell binding of certain cells may involve interaction with an integrin family of receptors.

Most studies with laminin have been carried out using laminin prepared from EHS tumor because of the difficulty of isolation from tissues. Although laminin prepared from EHS tumor is composed of the A, B1 and B2 chains, there are several studies which suggest that isoforms of laminin occur and function. For example, levels of mRNA for the A chain are found to be much lower in mouse tissues compared to mRNA levels of the B1 and B2 chains (Kleinman, H. K., et al (1987), Dev. Biol. 122, 373-378). Schwann cells produce laminin lacking the A chain (Palm, S. L., et al (1983), J. Cell Biol. 96, 1218-1226; Cornbrooks, C. J., et al (1983), Proc.

Natl. Acad. Sci. USA 80, 3850–3854). Although a variety of different activities of the A chain have been implicated, the exact function of the protein is still not clear. Study with synthetic peptides, domain specific antibodies, and expressing A chain cDNA in appropriate cells will clarify the functional role of the A chain.

Accordingly, the methodology for construction and isolation of the cDNA clones of the invention have been described in Example I above.

The nucleotide sequence and deduced amino acid sequence of the A chain of the murine laminin is shown in FIG. 4. FIG. 4 shows the nucleotide sequence and deduced amino acid sequence from laminin A chain cDNA. The predicted amino acid is shown below the cDNA sequence beginning at nucleotide 49. The cysteins and potential glycosylation sites are circled and underlined, respectively. In brief, cDNA is synthesized by oligo dT or specific primer extension using mRNA from either EHS tumor cell poly (A)+ RNA or differentiated F9 cell poly (A)+. The cDNA is inserted into the λgtll vector DNA followed by packaging and used to infect Escherichia coli. The resulting phage plaques are screened with either antibody to denatured laminin or radiolabeled DNA probes. cDNA inserts are then analyzed by Northern blotting and DNA sequencing. The predicted amino acid sequence agrees with the amino acid sequence of the proteolytic fragments of the A chain.

Figure 11:
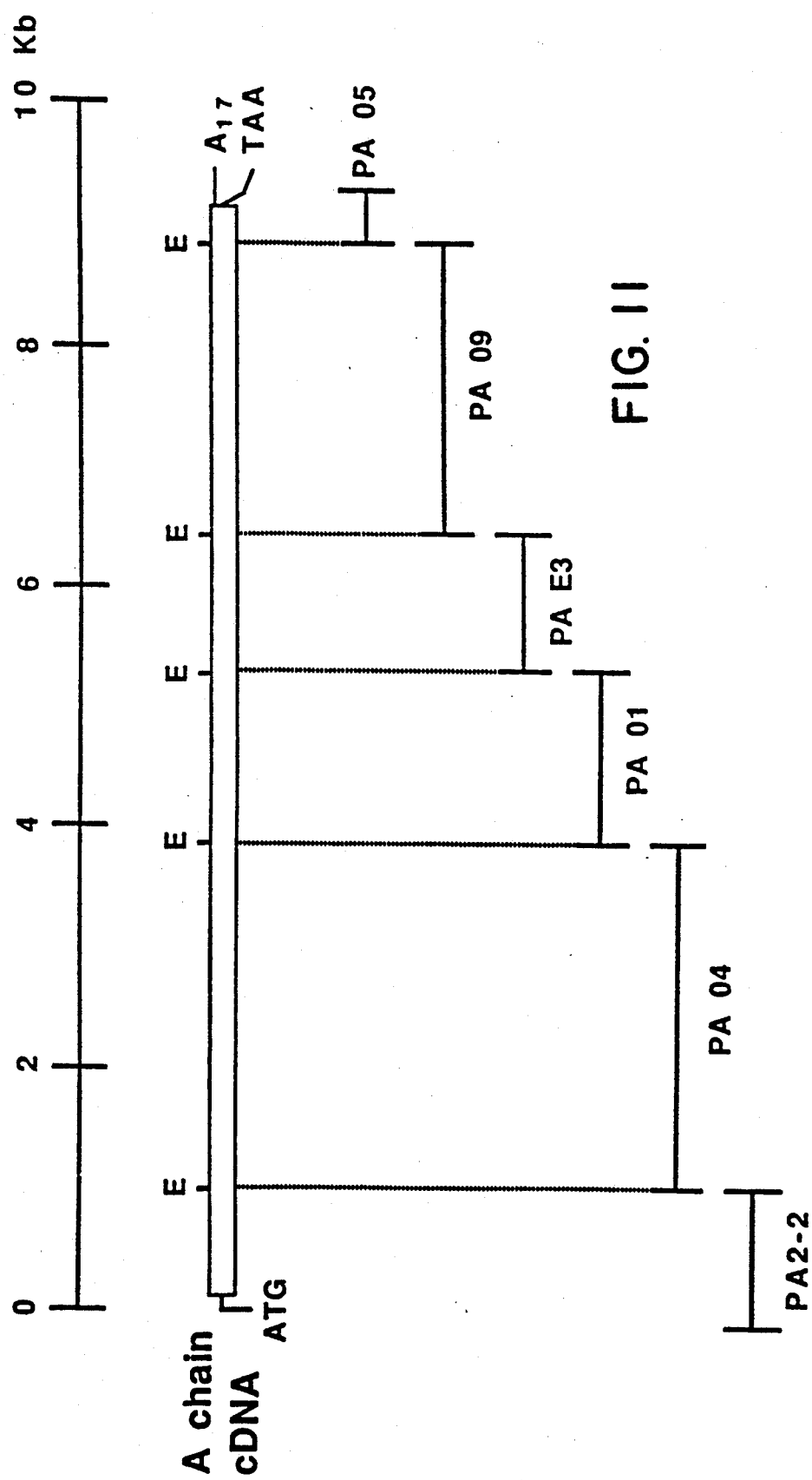
FIG. 11 shows cDNA clones which have been subcloned and code for the entire A chain of mouse laminin.

The EcoRI inserts of these cDNA clones encode for the entire A chain and are subcloned into PUC or pBR322 vector. These are PA05 (ATCC 67839), PA09 (ATCC 67835), PAE3 (ATCC 67837), PA01 (ATCC 67836), PA04 (ATCC 67840), and PA2-2 (ATCC 67838) and have been deposited with the ATCC (see FIG. 11). FIG. 11 shows the cDNA clones coding for the entire A chain of mouse laminin. The EcoR I cDNA inserts are subcloned into pBR322 or PUC vectors.

The cDNA inserts of the mouse A chain clones are used as probes to screen a human placenta poly (A)+ RNA cDNA library in the λgtll vector to isolate cDNA clones for the A chain of the human laminin. The positive clones are purified and DNA are prepared. DNA sequence is compared with the cDNA sequence for the mouse A chain to identify the clones.

Another aspect of the present invention provides a method for producing the novel polypeptide of the A chain. The method of the present invention involves culturing a suitable cell or cell line, which has been transformed with a DNA sequence coding for expression of a novel A chain polypeptide of the invention, under the control of known regulatory sequences. Suitable cells or cell lines may be mammalian cells such as Chinese hamster ovary cells (CHO) and the monkey COS-1 cell.

Bacterial cells are also suitable hosts. For example, the various strains of E. coli (ef. DH5, POP 036), B. subtilis, and Pseudomonas may be employed in this method.

Insect cells such as SF9 and many strains of yeast cells known to those skilled in the art are also employed as host cells for expression of the polypeptides of the present invention.

An additional aspect of the present invention provides vectors for use in the method of expression of these A chain polypeptides. The vectors contain either the full novel DNA sequences described above coding for the A chain of laminin or a segment of DNA coding a portion of the A chain. Additionally, the vectors also contain appropriate expression regulatory sequences.

A further aspect of the invention provides synthetic peptides from the deduced amino acid sequence of the cDNA sequence for the A chain. These synthetic peptides can be synthesized by any suitable method such as one previously used by our group (Graf et al (1987) Cell 48:989). A variety of synthetic peptides are tested for biological activity such as promoting cell adhesion, migration, growth and preventing invasion of tumor cells (see locations and sequences of the active peptides in FIG. 14 and Table III). FIG. 15 shows the effect of peptides on B16F10 Melanoma and HT-1080 cell attachment and spreading. A: increasing amounts of peptide were coated onto a 24 well dish in DMEM for 2 hours. The unbound peptide was removed and the wells were incubated with DMEM containing 3% BSA before the addition of cells. B and C: Morphological appearance of cells attached on peptide and laminin substrates. In the absence of peptides or laminin, few cells were attached. Table III is shown below.

TABLE III

| | Locations and sequences of active synthetic peptides | | |
|---|---|---|---|
| Peptides | Sequences | Length | Residues |
| PA21 | KCQAGTFALRGDNPQG | 16 | 1114–112 |
| PA36 | CSKCQAGTFALR | 12 | 1112–1123 |
| PA26 | XFALRGDNPQG | 11 | 1120–1129 |
| pA22-2 | XSRARQAASIKVAVSADR | 19 | 2091–2108 |
| PA22-3 | XRKQAASIKVAVS | 13 | 2094–2105 |
| PA22-4 | XIKVAVSADR | 10 | 2100–2108 |
| PA57 | XSRNLSEIKLLISRARK | 17 | 2080–2095 |
| PA32-1 | GLWNYIEREGKC | 12 | 2267–2278 |
| PA56 | KPLKTLEENLSRNLSEI | 17 | 2070–2086 |
| PA29 | DRLKPLKTLEENLSRNLSEI | 20 | 2067–2086 |
| PA31-1 | XGQIKKSPAVKVTHFKG | 17 | 2239–2254 |
| PA31-2 | XGQIKKSPAVKVT | 13 | 2239–2250 |
| p10A | CIRAYQPQTSSTNYNTLTIL | 19 | 2110–2128 |

The underlined residues designated by an X can be an amino acid such as cysteine. The X residue is not present in the original A chain sequence but is added as desired. For instance, an X group such as a cysteine addition to the authentic sequence allows for the coupling of the peptide to other materials. Thus, the cysteine may be used for coupling with other proteins. Moreover, when X is a glycine derivative such as bromoacetylglycineglycine, it is used for polymerization of the peptide and cyclization of the peptide. To obtain polymerized material the bromoacetyl-glycine-glycine is incubated overnight at 50 mg/ml at neutral pH. Cyclized material is obtained by similar incubation but at 1 mg/ml.

The invention also involves chemical modification (e.g. cyclization of the peptide or covalent coupling to another molecule) including combining the peptide of the invention with another protein such as albumen which is relatively biologically inert.

An additional aspect of the present invention is that the peptide can be coupled to an inert support and used to isolate the cell surface receptor for this peptide. The receptor is isolated by conventional affinity chromotography (Kleinman et al (1988) Proc. Natl. Acad. Sci USA. 85:1282).

Figure 12:
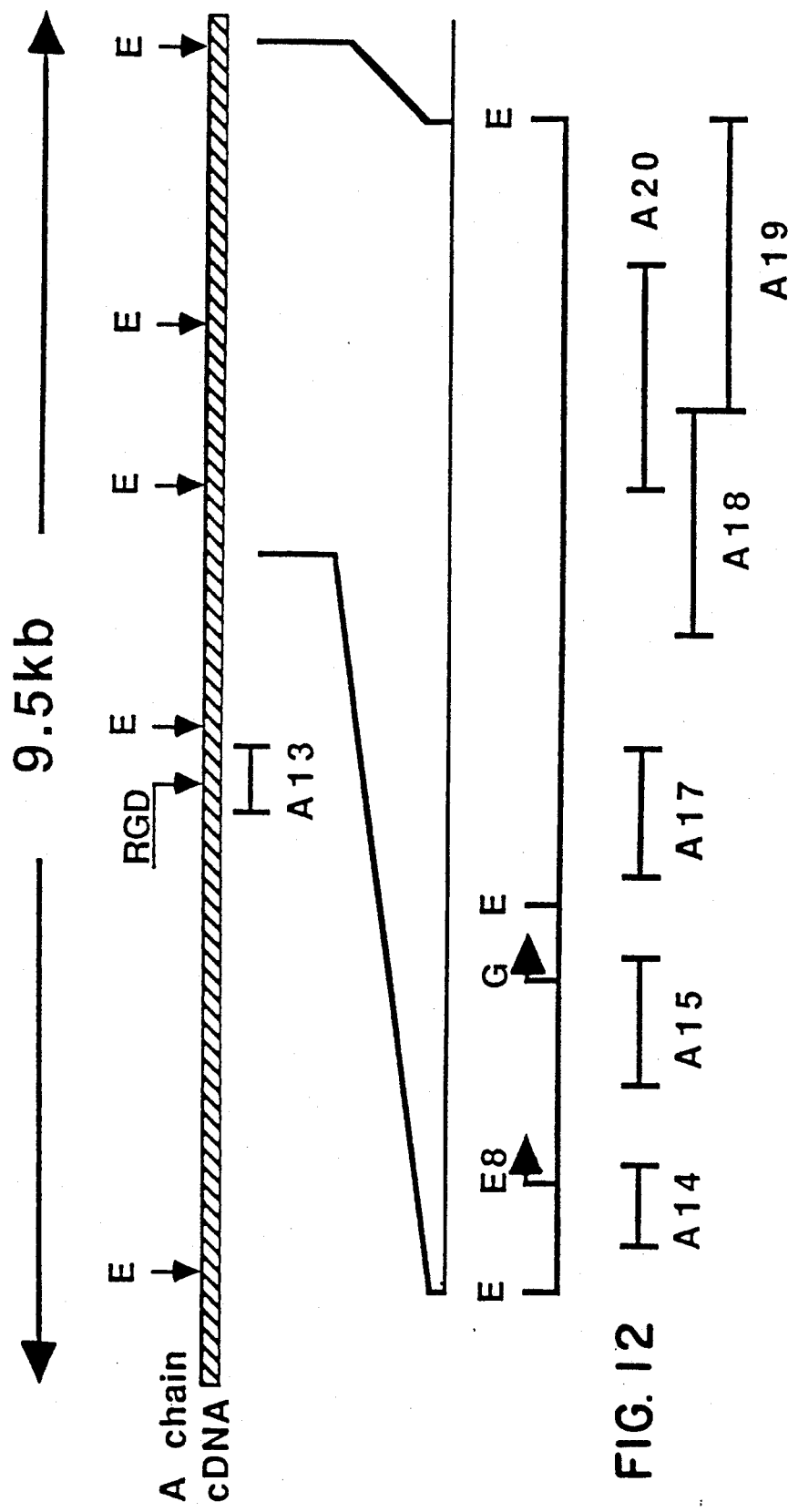
FIG. 12 shows the location of cDNA segments used to generate fusion proteins.

An additional aspect of the invention is a therapeutic method and composition for promoting cell adhesion, migration, differentiation, and preventing tumor cell metastasis. Such a composition comprises a therapeutically effective amount of a synthetic peptide or polypeptide, preferably 1 ug to 1 mg. Further therapeutic methods and compositions of the invention comprise a therapeutic amount of a synthetic peptide or polypeptide of the A chain with a therapeutic amount of at least one of the different synthetic peptide of the invention. Additionally, the proteins according to the present invention or a combination of the proteins of the present invention may be co-administered with one or more different synthetic peptides or with the peptide from the different proteins with which it may interact. The invention also includes locally administering the composition as an implant or any part of it either alone or bound to a synthetic material, such as a vascular prostheses or nerve guide.

The compositions of the invention will hereinafter be described in greater detail.

The peptides of the present invention can be made into pharmaceutical compositions by combination with appropriate medical carriers or diluents. For example, the peptides can be mixed with starch, sugars and other inert ingredients commonly used to make nerve guides and used as surgical implants for nerve regeneration. Tablets may also be prepared for oral application. The peptides can also be dissolved in oils, propyleneglycol or other solvents commonly used to prepare injectable solutions. For topical application, they can be formulated as ointments or creams.

More specifically, the peptides of the present invention may be formulated into preparations in solid, semisolid, liquid (e.g. eye drops) or gaseous form such as tablets, capsules, powders, granules, ointments, solutions, suppositories, and injections, in usual ways for oral, parenteral, or surgical administration.

The following methods and excipients are merely exemplary and in no way limit the invention.

The peptides of the present invention in pharmaceutical dosage forms may be used in the form of their pharmaceutically acceptable salts, and also may be used alone or in appropriate association, as well as in combination with other pharmaceutically active compounds.

The peptides in the case of the preparation of surgical (e.g. nerve guide) implants may be used alone in a polymerized form or combined with appropriate additives to make a flexible guide. Suitable additives include collagen, polylacetate or other biodegradable and biocompatible compounds. The peptides in the case of oral preparation may be used alone or combined with appropriate additives to make tablets, powders, granules or capsules, e.g. with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; with lubricants such as talc or magnesium stearate; and if desired, with diluents, buffering agents, moistening agents, preservatives and flavoring agents.

The peptides of the present invention may be formulated into preparations for injections by dissolving, suspending or emulsifying them in aqueous solvents such as normal saline, Dextrose 5%, or non-aqueous solvent such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers and preservatives The peptides of the invention may be combined with other compounds such as with other active agents.

Application of the ability of the invention to inhibit cell attachment when presented in a solubilized form may find utility in situations where it is desirable to prevent cell adhesion to a substrate or adhesion between cells. Undesirable cell attachment to various medical sutures, or dressings, may be prevented by presenting the invention in solubilized form. When the invention is used either in conjunction or combination with another molecule, such as a therapeutic agent, or particle treated with such an agent, the entrance of that agent or particle into the cell may be enhanced by the effect of the invention on the phagocytic activity of the cell, thereby increasing the efficiency of the therapeutic agent.

The following example further illustrates the composition of the present invention and will enable others skilled in the art to understand the invention more completely. It is understood that the invention is not limited to the Example below.

EXAMPLE 2

1 mg of the active peptide is polymerized and mixed with 5 mg of collagen and processed to form a thin tube. The thin tube is then implanted at the site of nerve damage in a subject.

Methods of treating various diseases or disorders with the compound or composition of the invention will hereinafter be described in greater detail.

Methods for preparing bio or cell compatable surfaces

The peptide can be coupled to plastic surfaces for in vitro use for cell culture or to prostheses such as a vascular prostheses (Gortex etc.) or an artificial heart to make the synthetic materials more biocompatible and allow for cells to adhere and grow. In the case of tissue culture (in vitro use), the surface of a 16 mm diameter culture well can be modified to covalently link the peptide to the plastic surface. Here from 50 ng to 1 ug per 16 mm diameter disk would be recommended based on current experiments. For prostheses to be used in vitro, it may be possible to incorporate the peptide into the polymer or as above and activate the surface and allow the peptide to covalently link to the polymer. In order to obtain desirable effects, generally it is recommended to have between 50 ng and 5 ug per $cm^2$ based on current experiments.

EXAMPLE 3

The prostheses, culture dishes and nerve guides can be formulated with the peptide of Example 8. The nerve guide may be surgically administered to a patient.

The desirable dose of the peptides of the present invention varies with the subject, drug form, method and period of administration. Modes of administration include intravenous and parenteral administration. The maximal dose for a mouse is 1 mg/10 gm body weight and the lower amount is 0.1 mg.

EXAMPLE 4

Expressing cDNA in Bacteria

A variety of segments of cDNA for the A chain were inserted into a cloning site of a vector PEX to generate a $\beta$-galosidase fusion protein containing a portion of the A chain. FIG. 12 shows the locations of the inserts used in these experiments. The recombinant plasmids were then transformed into *E. coli* strain pop 2136 which carries the gene coding for the Clts 857 repressor.

Furthermore, FIG. 12 shows the location of cDNA segments used to generate fusion proteins. Fragments A13, 14, 15, 17, 19, 20 are inserted at polylinker sites of PEX expression vector to generate β-galactosidase fusion proteins. E represents EcoR I sites. E8 and G indicate the start site of the proteolytic fragment E8 and domain G.

In the PEX expression, plasmid expression of the fusion protein can be controlled by temperature. The bacteria carrying the recombinant plasmid were grown at 30 degrees C. until a cell density of $2 \times 10^8$ cells/ml and then the cultures were incubated at 42° C. for 2 hours. At 42° C. the CI repressor is inactivated and fusion protein accumulates to levels of up to 20% of the total $E.\ coli$ protein. After a 2 hour incubation, the cells (20 ml culture) were precipitated, resuspended in 1 ml Tris-HCl containing 0.15 M-NaCl and 5 μg/ml lysozyme. The cells were lysed by sonication for several times and by lysozyme and were centrifuged at 13,000 pm for 10 minutes. The precipitate was resuspended in 1 ml 7M urea and dialysed against 0.05M Tris-HCl, pHI7.5. At this step, the purity of the fusion protein is about 95%. The protein was then used to immunize a rabbit.

EXAMPLE 5

Expression of the A chain in insect cells

A helper-independent baculovirus expression vector developed by Smith et al (Smith G., et al (1985), *Proc. Natl. Acad. Sci.* USA 82: 8404–8408) has been used for the expression of a wide variety of heterologous genes. The baculovirus vector utilizes the highly active *Autographa californica* nuclear polyhedrosis virus (AcMNPV) polyhedrin promoter modified for the insertion of the foreign gene. The advantage of the vector is the very abundant expression of recombinant proteins, which is in many cases, are antigenically, and functionally active. Cultured insect cells (SF9) were transfected with a mixture of baculovirus DNA and recombinant plasmid DNA (see FIG. 13).

Figure 13:
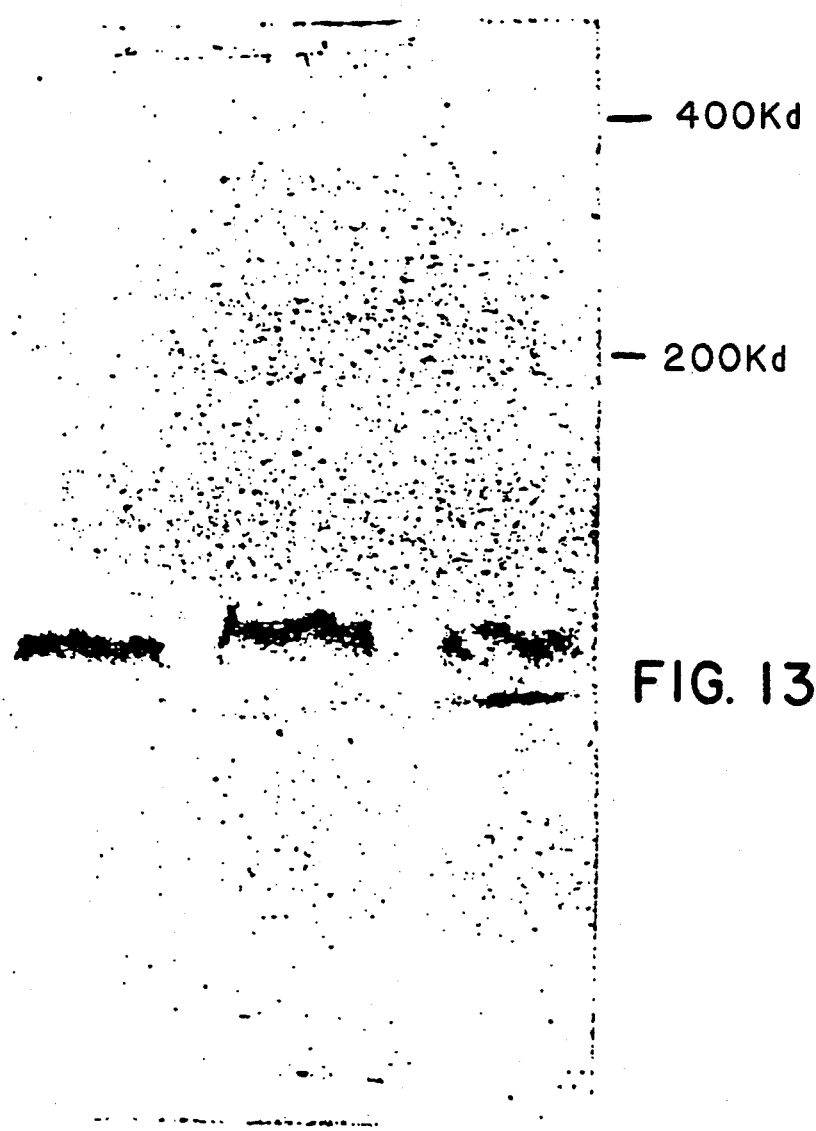
FIG. 13 shows the Western blot of a segment of the A chain expressed in insect cells.

FIG. 13 shows a Western blot of a segment of the A chain expressed in insect cells. The resultant virus progeny are plated at 100–1000 plaques per plate. Viral recombinants were identified by DNA hybridization and purified to homogeneity. The recombinant virus was then expanded and used to produce the recombinant protein.

Figure 14:
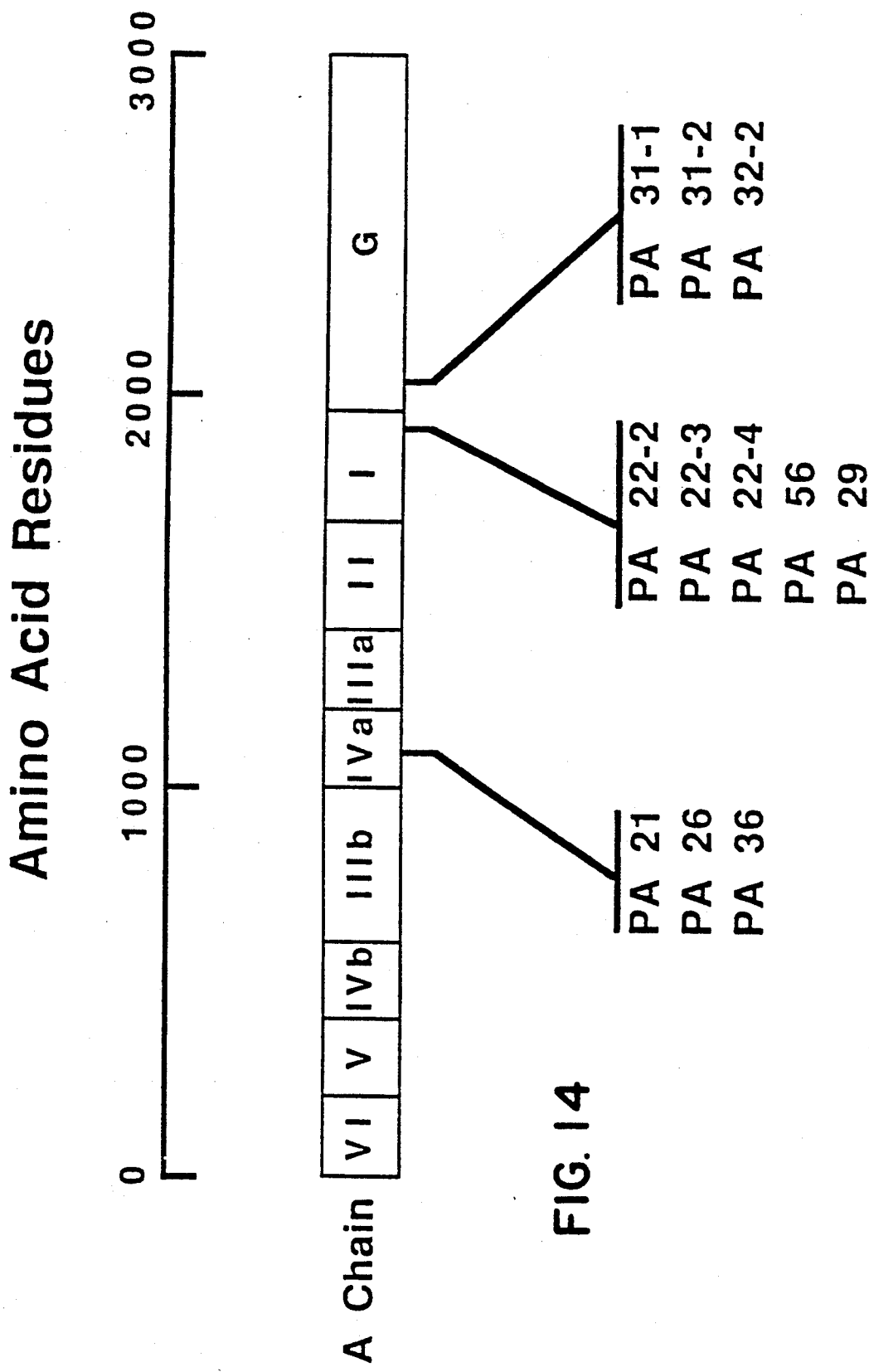
FIG. 14 shows the relative locations of active synthetic peptides in the A chain.

FIG. 13 shows an example of the protein which was analyzed by western blotting using polyclonal antibody to laminin. FIG. 14 shows the relative locations of active synthetic peptides in the A chain. Numerical numbers and G represent domains.

EXAMPLE 6

Active peptide PA222-2 and its derivatives

Figure 16:
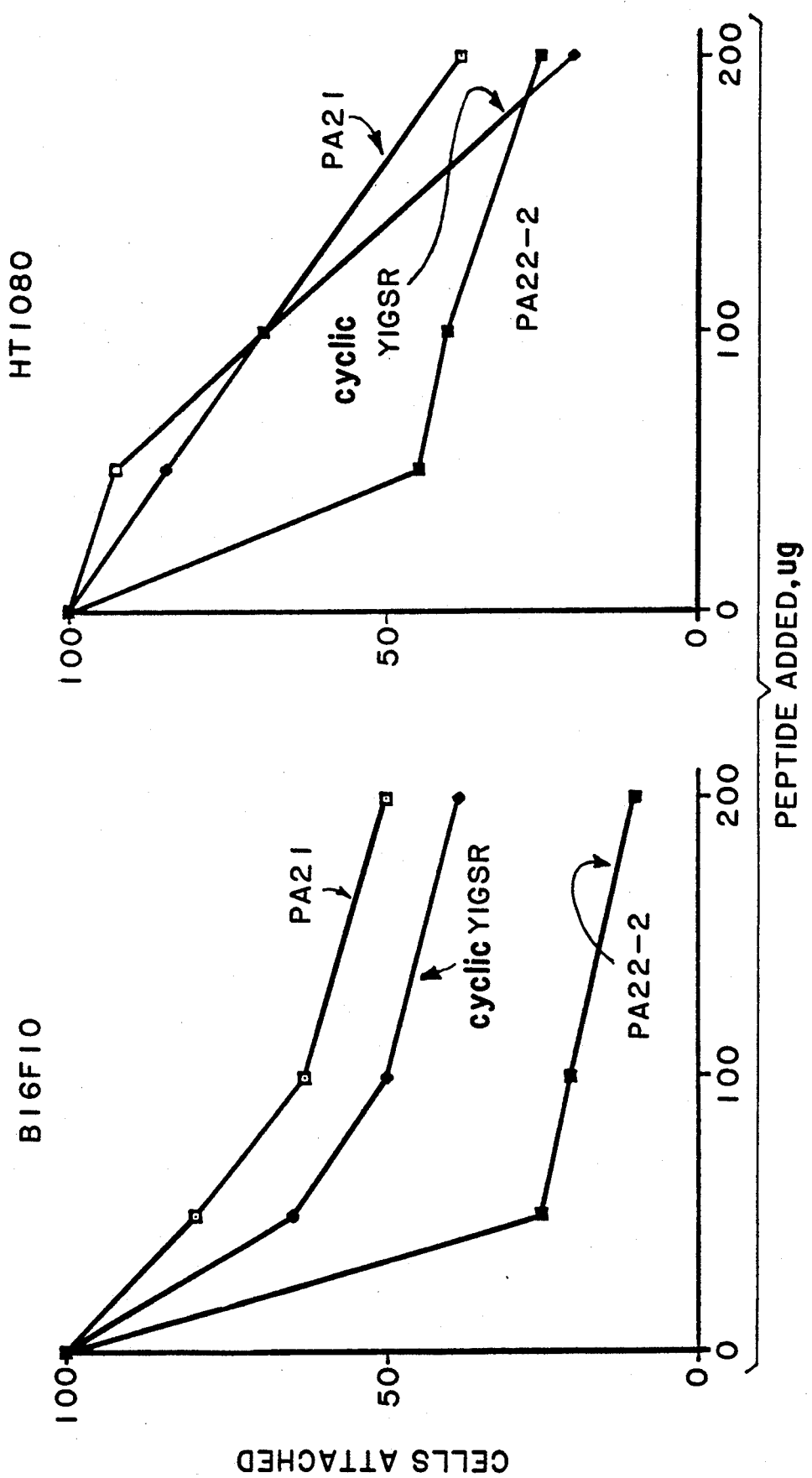
FIG. 16 shows the effect of peptides on blocking laminin-mediated cell attachment.

A synthetic peptide designated PA22-2 and its derivatives PA22-3, PA22-4 (see sequences and locations in Table II and FIG. 16 have been prepared in our laboratory (as previously described Graf et al (1987) Cell 48: 989) and tested (see below) for various biological activities. The following data document all of the presently found activities for this peptide with cells in culture and tumor cells in vivo. Since all three peptides are almost equally active, the data obtained with PA22-2 are shown here.

(A) Adhesion

Figure 15A:
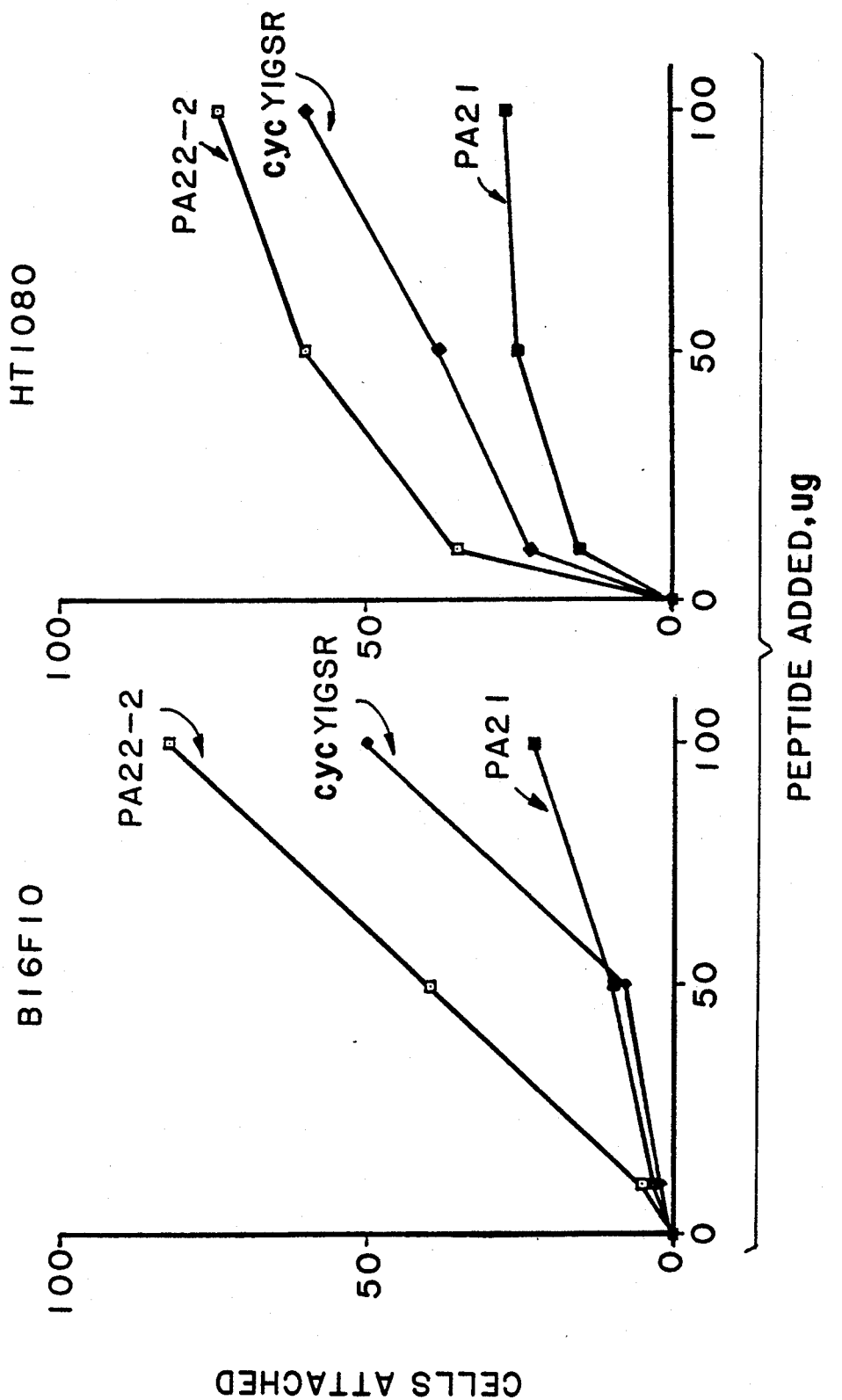
FIGS. 15A-C show the effect of peptides on B16F10 Melanoma and HT-1080 cell attachment and spreading.
Figure 15B:
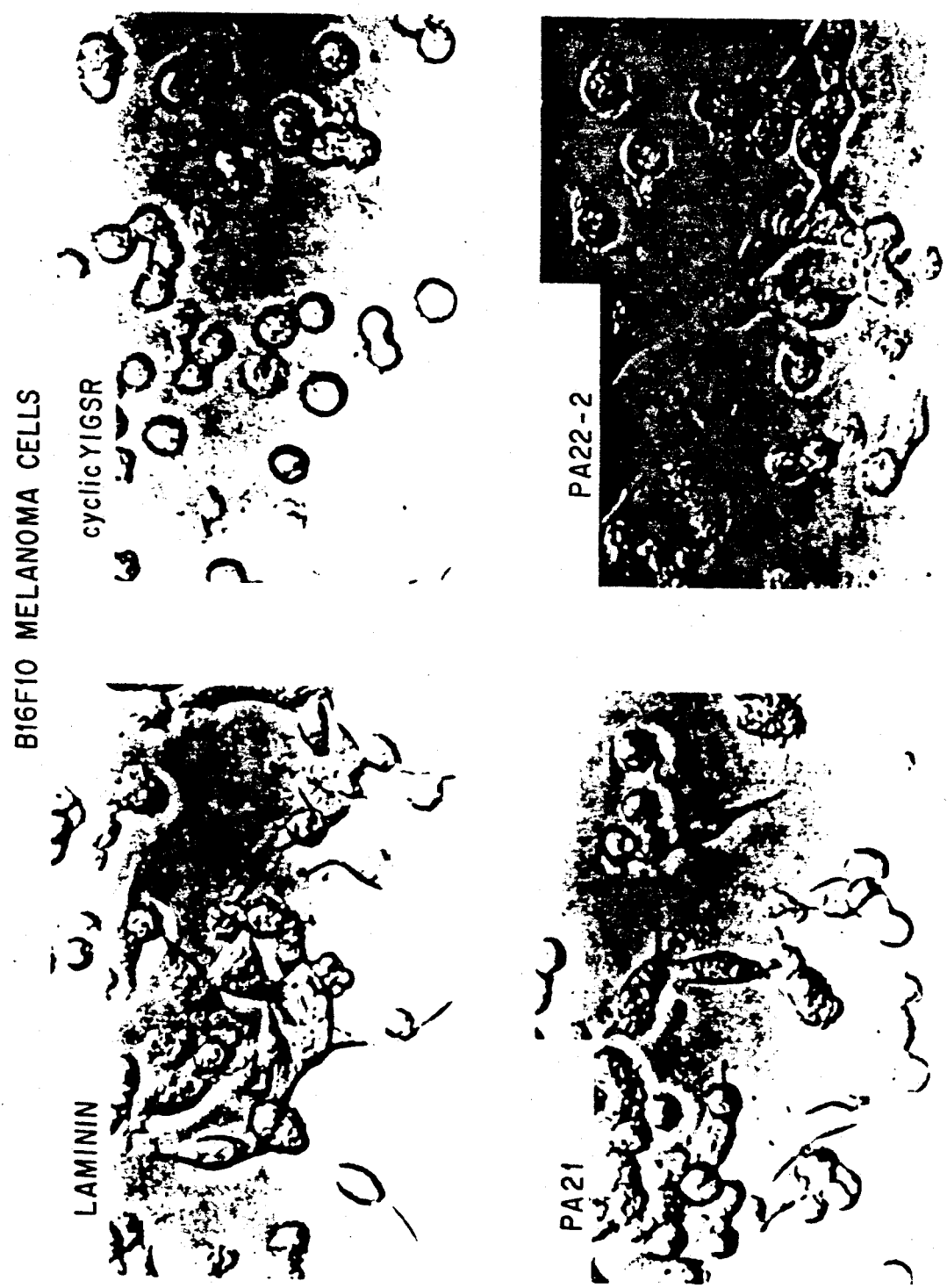

When the peptide (PA22-2) is coated onto a plastic dish it promotes the adhesion of various epithelial cells in a rapid dose-dependent manner (see FIG. 15A). This peptide is active with various cells and its activity can be equal to that of laminin itself in terms of the total number of cells that can attach to surfaces coated with the peptide. It is as active or more active than a previously described peptide (YIGSR) (see Table IV). Table IV is shown below.

TABLE IV

| cell type | Laminin Attachment | Laminin Spread | cyc-YIGSR A | cyc-YIGSR S | PA 21 A | PA 21 S |
|---|---|---|---|---|---|---|
| B16F10 (melanoma) M2 | ++++ | ++++ | ++ | − | ++ | + |
| | ++++ | ++++ | + | + | +++ | +++ |
| C110 (fibrosarcoma) | ++++ | ++++ | +++ | + | ++++ | ++++ |
| | ++++ | ++++ | +++ | − | ++ | + |
| HT1080 (fibroblast) | | | | | | |
| 3T3 | − | − | − | − | +++ | + |
| ras-3T3 | − | − | + | ± | ++++ | ++ |
| NRK | ++++ | ++++ | + | ± | +++ | +++ |
| WI-38 | ++++ | ++++ | + | ± | + | + |
| (myoblast) H9C2 | ++++ | ++++ | + | − | + | − |
| KCNR | ++++ | + | ++++ | − | − | − |
| (neuron BE2 cell) | ++ | + | ++++ | − | + | − |
| NG108 | ++++ | ++++ | ++++ | − | +++ | + |
| PC12 | | | | | | |
| NGF − | | +++ | +++ | +++ | − | + | − |
| NGF + | | ++++ | +++ | ++++ | − | + | − |
| (ovary cell) OV3 | ++++ | − | + | − | + | − |
| CHO | + | − | ++ | − | + | − |
| (endothelia) cell HUVEC | +++ | +++ | + | ± | ++ | +++ |
| (epidermal) cell PAM212 | − | − | + | − | + | ± |
| (embryonal) carcinoma F9 | ++++ | ++++ | ++ | ± | ++++ | + |
| (pancreas) carcinoma Capan | ++++ | − | − | − | − | − |
| pys2 | ± | − | + | − | ++ | +++ |

Figure 15C:
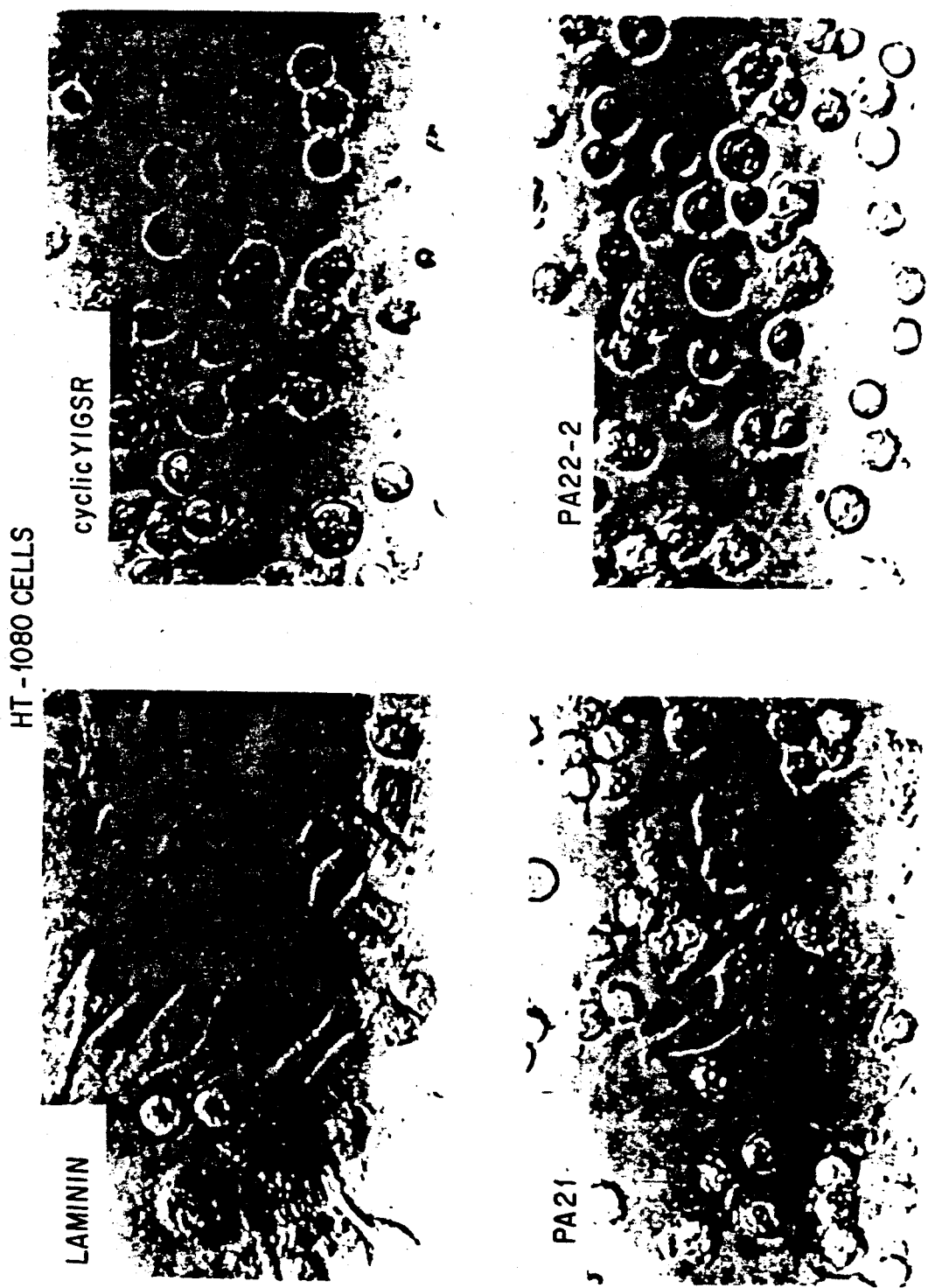

With some cells such as B16F10 spreading is observed on substances coated with the peptide (see FIG. 15B) whereas with other cells such as HT-1080 spreading is not observed (see FIG. 15C). In addition, the peptide can complete (i.e. block) laminin-mediated cell adhesion (see FIG. 16) suggesting that for many cells it is the major active site on laminin for cell adhesion. FIG. 16 shows the effect of peptides on blocking laminin-mediated cell attachment. Laminin was coated on the dish as described above, then peptide togehter with cells were added to the dishes and cell adhesion after one and a half hours was determined.

(B) Neurite Outgrowth

Laminin is very active in promoting neurite outgrowth for both peripheral and central neurons in vitro. In vivo it has been shown to promote the regeneration of sciatic and optic nerve. In fact, laminin promotes regeneration faster and over greater distances than any other factor described to date. Peptide PA22-2 when coated on a plastic dish mimics the neurite promoting activity of laminin. It is active in a dose-dependent manner and is active both with neural cell lines (PC-12 FIGS. 17A and B and NG108-15) and with primary cultures of neural cells both from the peripheral and the central nervous system. The processes formed appear identical to those observed with intact laminin (see FIG. 17A).

Figure 17B:
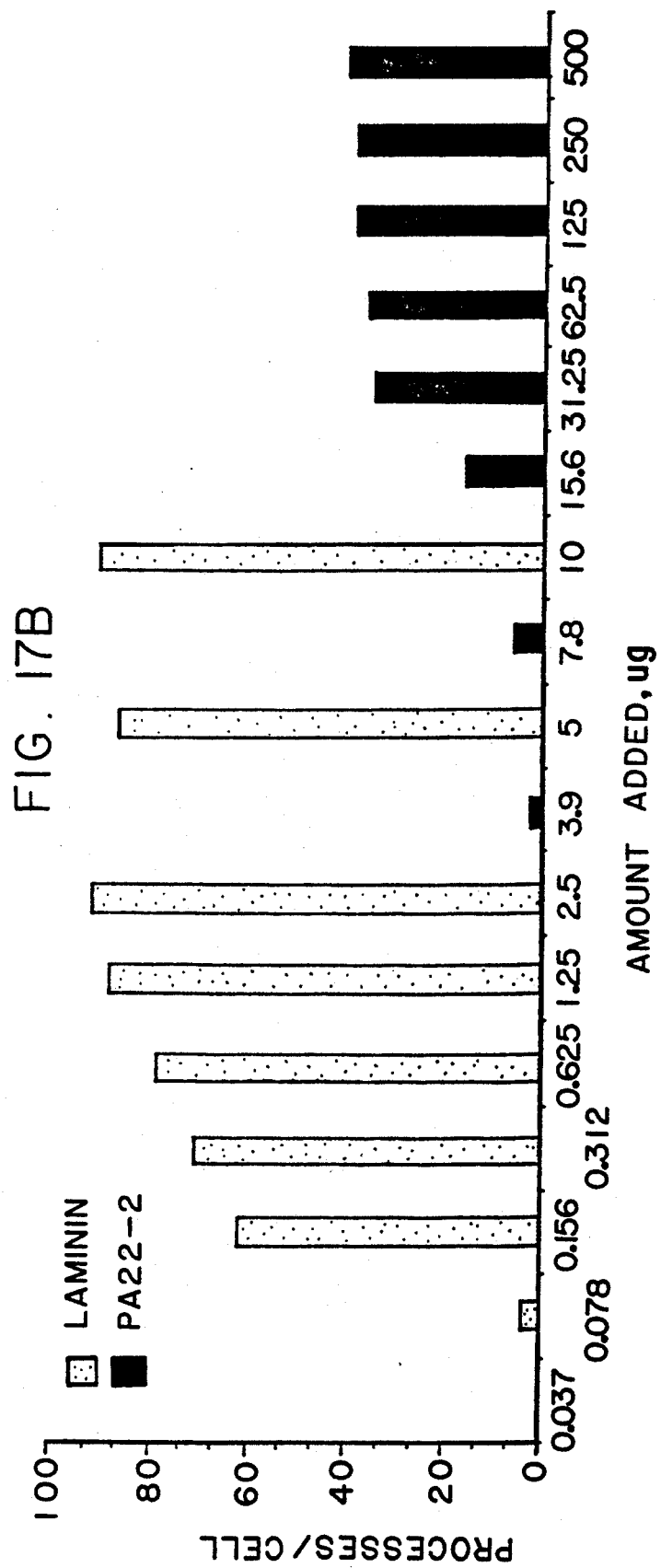

FIG. 17 shows the effect of peptide PA22-2 on promoting PC12 process formation relative to laminin. The assay was carried out in a similar manner to the cell adhesion assay. 17A: Morphology after 4 hours. 17B: Dose response curve showing number of processes formed. Cells were directly counted from at least 10 microscopic fields.

(C) Cell differentiation

Figure 18B:
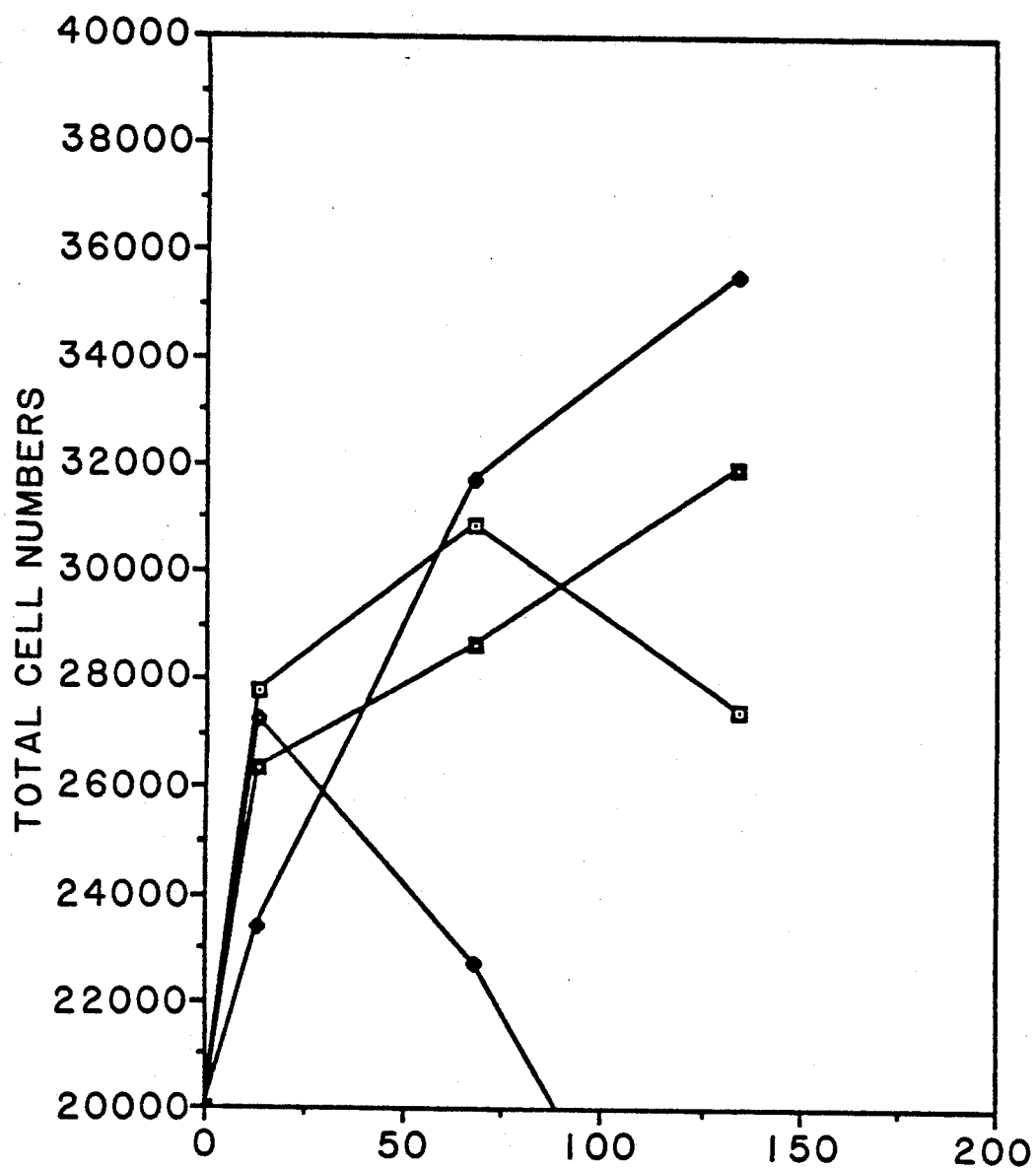
Figure 18C:
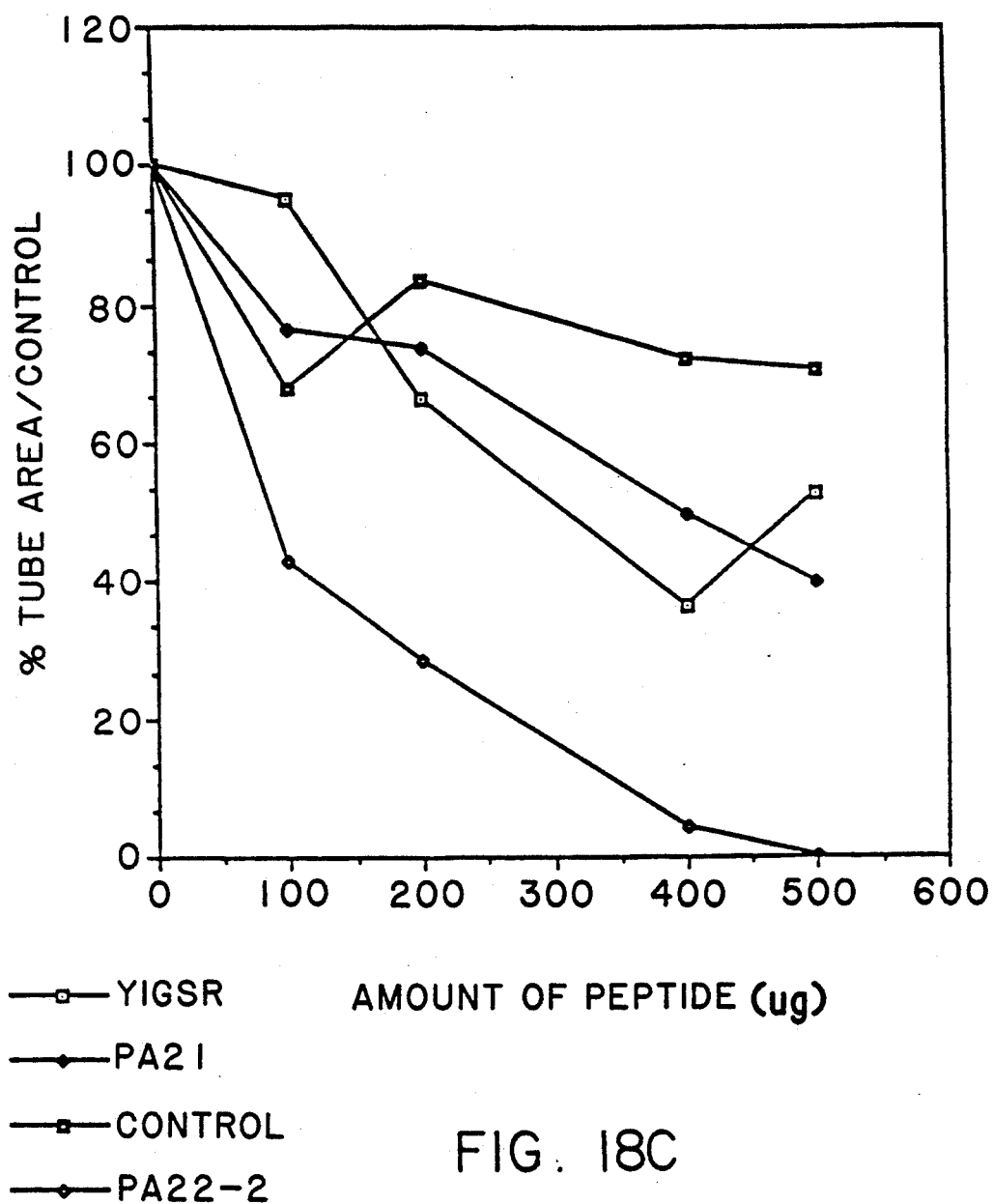

Human umbilical vein endothelial cells when coated on a reconstituted basement membrane substrate rapidly (by 12 hours) organize into capillary-like structures (see FIG. 18A). The peptide PA22-2 does not alter the adhesion of these cells (see FIG. 18B) but does block the formation of capillary-like structures (see FIGS. 18A and 18C). It is the most potent of all the peptides tested and is active in a dose-dependent manner. It may have a potential clinical use in blocking blood vessel formation as for example, during the vascularization of tumors and in diabetic retinopathy (ex diabetic retinopathy or Kaposi sarcoma). Thus, FIG. 18 shows the effect of synthetic peptide on human umbilical vein endothelial cell adhesion and tube formation. 18A: Morphology of cells. Cells were plated on a reconstituted basement membrane substrate and after 2 and 18 hours it is apparent that the cells line up into capillary-like structures. Peptide PA 21 and PA22-2 when added either with the plated cells or 18 hours later both block this effect. 18B: Adhesion to peptides. 18C: peptide inhibition of tube formation.

(D) Collagenase Induction

Figure 19:
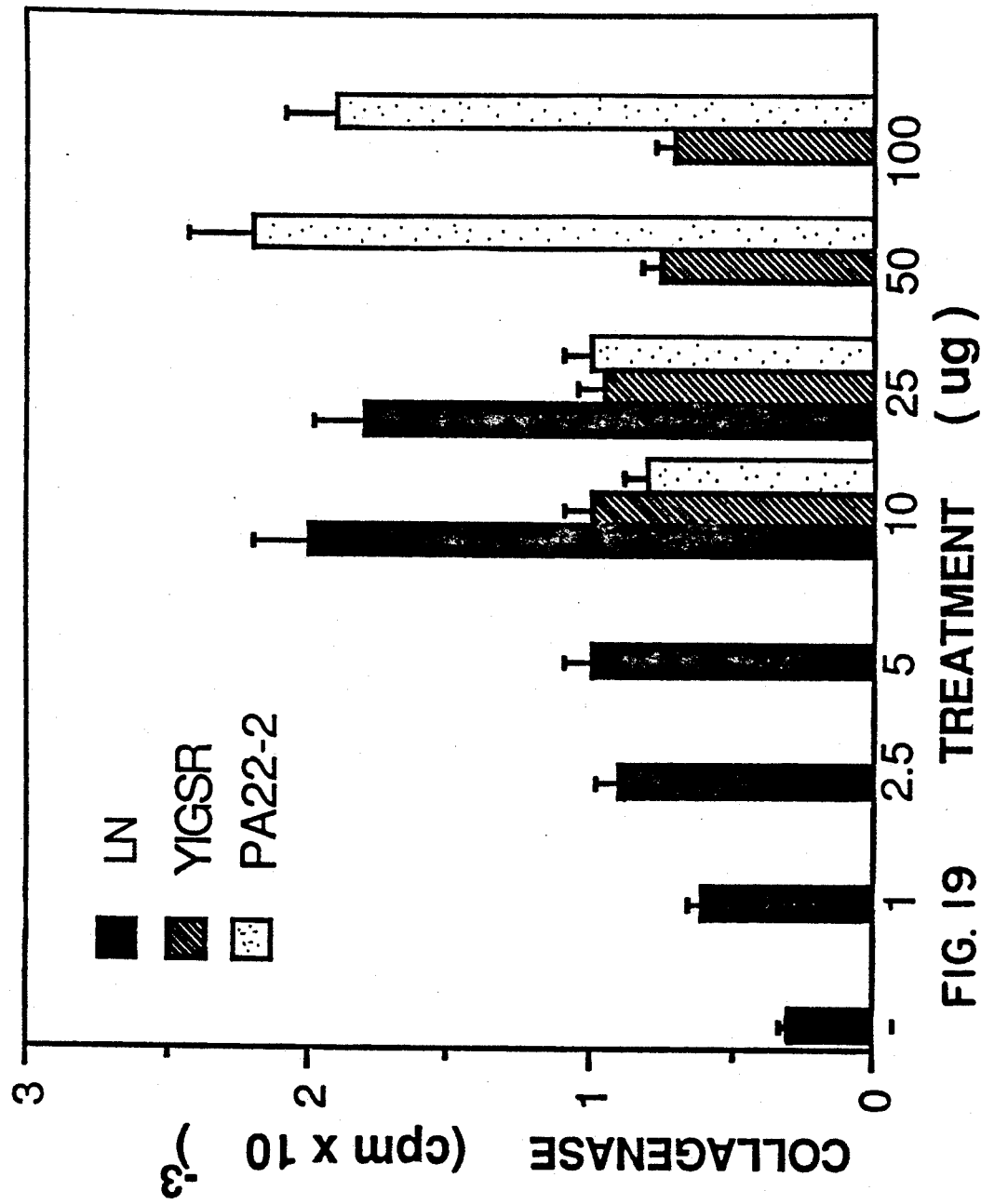
FIG. 19 shows the effect of peptides PA22-2 and YIGSR and laminin on collagenase production by HT-1080 cells.

It has been shown that intact laminin induces the production of collagenase IV, an enzyme necessary for the breakdown of type IV collagen, the major structural element in basement membranes. This enzyme is thought to be important in cancer where its production is correlated with the invasive and metastatic activity of malignant tumor cells. In fact, degradation of basement membranes by collagenase IV is a necessary step in the metastatic process. Incubation of HT-1080 fibrosarcoma cells with peptide PA22-2 results in an increase in the production of collagenase to levels comparable to those observed with intact laminin (see FIG. 19). FIG. 19 shows the effect of peptides PA22-2 and YIGSR and laminin on collagenase production by HT-1080 cells. The cells were treated for 6 hours with various amounts of the peptide and then the conditional medium was assayed for the production of collagen IV degrading enzymes. The effect is dose-dependent and is not reproduced by any other peptide tested to date. The importance of localizing this activity to peptide PA22-2 is that it will now be possible to more precisely define the molecular events involved in the metastatic process. Competitive inhibitors of this activity can be readily designed by modification of the composition of the active peptide i.e. Dasmano acids, cyclic forms etc. There may also be situations where the production of the enzyme could be advantageous such as in speeding the migration of leukocytes to sites of infection.

(E) Tumor formation

It is well known that tumor cells must attach degrade, and migrate through basement membranes in order to spread to distant sites. Laminin is known to increase the metastic phenotype of tumor cells and the number of tumors formed in mice. Using a line of B16 melanoma cells which specifically colonize the lung when injected into mouse tail vein, we have studied the effect of peptide PA22-2 on the formation of lung tumors.

In these studies, various amounts of peptide PA22-2 are mixed with the B16F10 melanoma cells ($5 \times 10^4$) and injected into mice via the tail vein. Eight mice are injected for each concentration of test peptide. After 2-3 weeks, the mice are sacrificed and the number of segmented colonies on the lung surface are counted. Peptide PA22-2 (1 mg/mouse) causes a two-fold increase in the number of lung tumors (see Table V and FIG. 20).

TABLE V

Lung Tumor formation After Injection of
B16F10 Melonoma Cells in The Presence
and Absence of Laminin peptides

| Peptide Injected | Number of Tumors/animal |
| --- | --- |
| None | 26 |
| Cyc YIGSR (1 mg) | 4 |
| PA22-2 (0.5 mg) | 44 |
| PA22-2 (1.0 0 mg) | 53 |

$10^5$ melanoma cells in a final volume of 0.2 ml of Dulbecco's modification of Eagle's medium (DMEM) containing the indicated amount and type of peptide were injected in the tail vein. Eight mice were in each test group. After 3 weeks, the mice were sacrificed, lungs were removed. The number of tumors on the surface of the lungs was determined by using a microscope.

Figure 20:
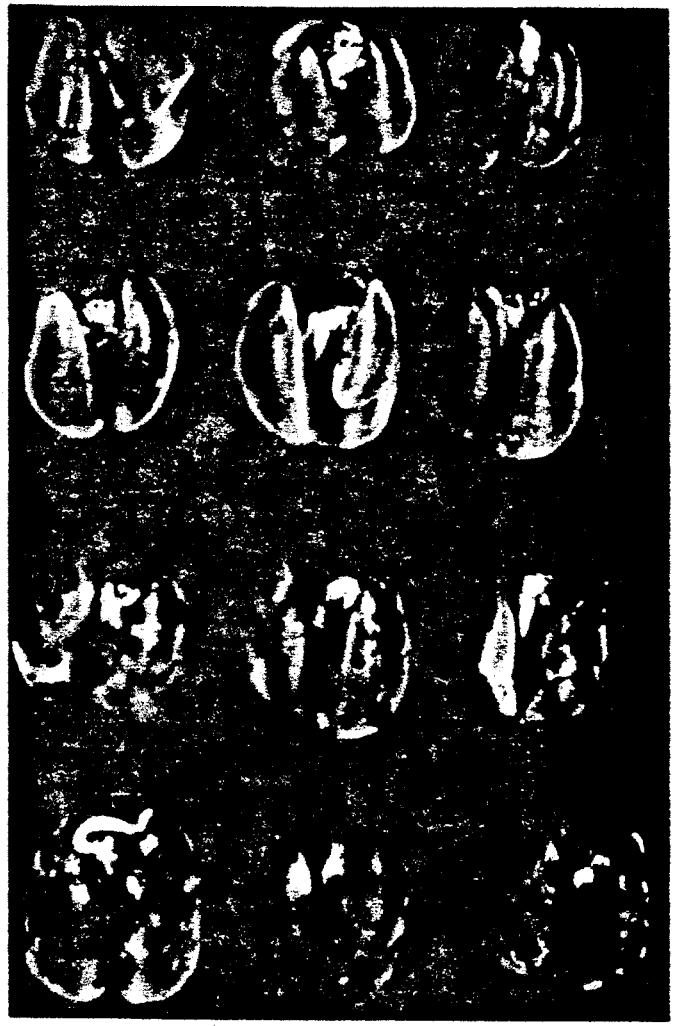
FIG. 20 shows the effect of YIGSR and PA22-2 on the formation of lung colonies by Melanoma cells.

FIG. 20 shows the effect of YIGSR and PA22-2 on the formation of lung colonies by Melanoma cells. Each group contained 8 mice which were injected with $7.5 \times 10$ B16F10 Melanoma cells via the tail vein in a final volume of 0.2 DMEM containing the designated amount of peptide. After three weeks, the animals were sacrificed and the number of colonies on the surface of the lungs was determined.

The effect is dose-dependent and opposite to that of another previously described peptide YIGSR which blocks tumor formation. The significance of this finding is that it allows one to modulate the metastatic process and develop inhibitors based on the known composition of the active peptide

(F) Cell Growth

Our results suggest that P22 and its derivatives stimulate growth of B16-F10 and PC12 cells.

(G) Heparin binding

Our results suggest that P22 and its derivatives promote activity to bind heparin.

EXAMPLE 7

Active peptide PA21 and its derivatives

A sequence from the different portion of the A chain of laminin has also been found to be biologically active. It has been tested in various assays and has activities distinct from those observed with the previously reported peptide YIGSR from the B1 chain and distinct from peptide PA22-2 which is located near the carboxyl end of the A chain. PA21 and its derivatives PA36, PA26 are shown in Table III and the data below are examples of its biological activity which we have documented to date.

PA21 and PA26 when coated on plastic surfaces support the attachment of many cells (see FIGS. 15, 18A and Table IV). Many of the same cells which recognize peptide PA22-2 and YIGSR also recognize and bind to PA21 and PA26 but the degree of binding is quite different. For example, peptide PA21 binds endothelial cells most strongly (see FIG. 18). Since peptides PA21 and PA26 contain an RGD sequence which is a potential binding sequence for integrin type of receptors, many cells are expected to bind to these peptides In contrast, PA36 encompasses the amino terminal half of PA21 and does not have the RGD sequence. Since the sequence of PA36 is unique to laminin, the response of endothelial cells to PA36 is likely to be specific to the peptide. PA36 also effectively competes with intact laminin for endothelial cell binding to laminin whereas the other peptides are much less active. PA21 has some activity in preventing tube formation by endothelial cells (comparable to YIGSR) but is less active than PA22-2 (see FIG. 18A). PA21 does not induce collagenase or have any effects on tumor formation in mouse lungs. Because PA36 is specifically active with endothelial cells for cell adhesion, it may eventually have clinical uses such as coating vascular prostheses to ensure a rapid covering of the surface with endothelial cells. Currently, the surfaces of such implants do not readily cover with endothelial cells and therefore are often thrombogenic with the potential of creating blood clots.

EXAMPLE 8

Active peptide pA32-1

Figure 21:
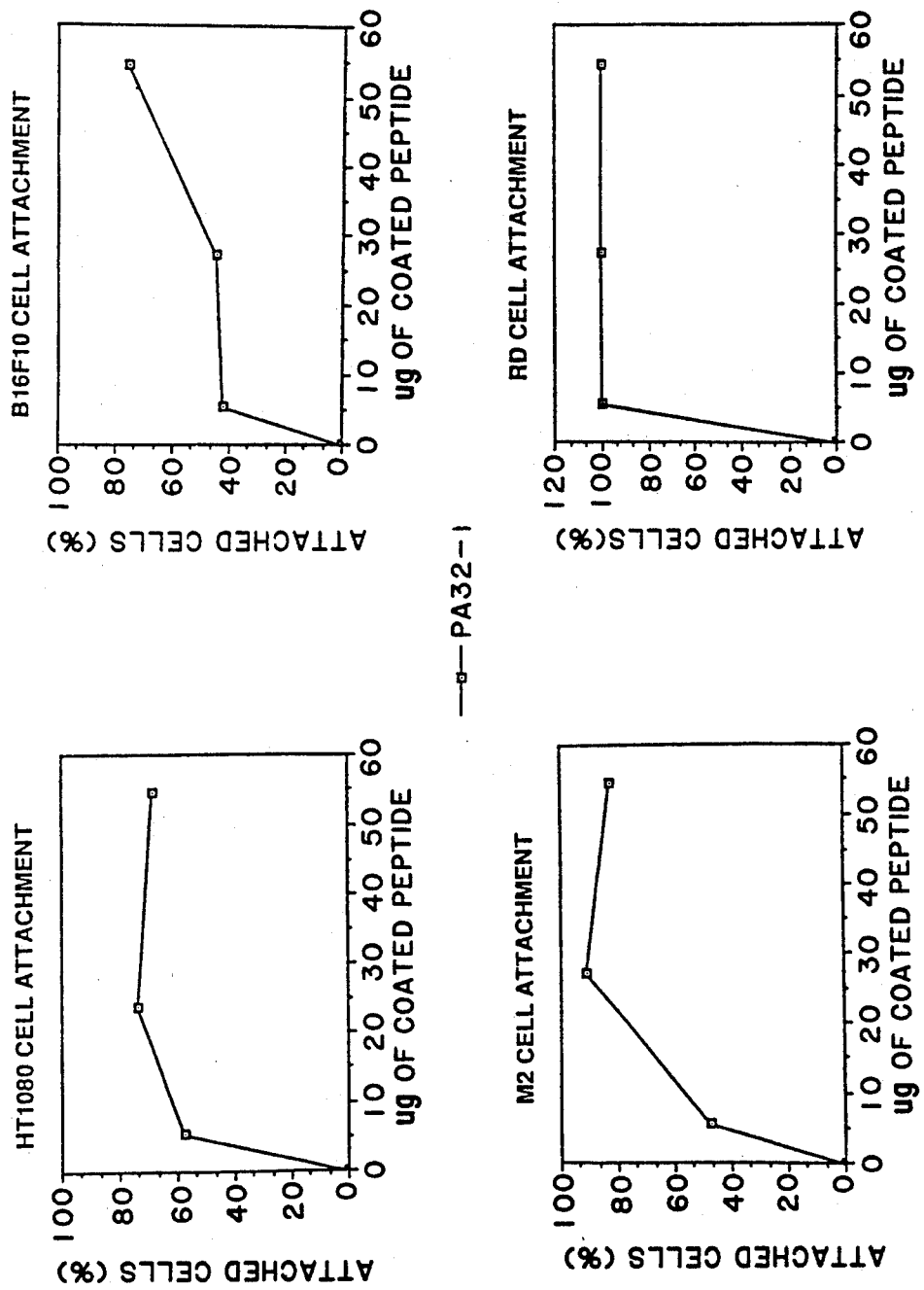
FIG. 21 shows the adhesion to peptide PA32-1.

The location and sequence of peptide pA32-1 are shown in FIG. 14 and Table III. This peptide is active in cell attachment as shown in FIG. 21. The peptide is also active in heparin binding.

EXAMPLE 9

Active peptide pA56 and its derivative

Figure 22:
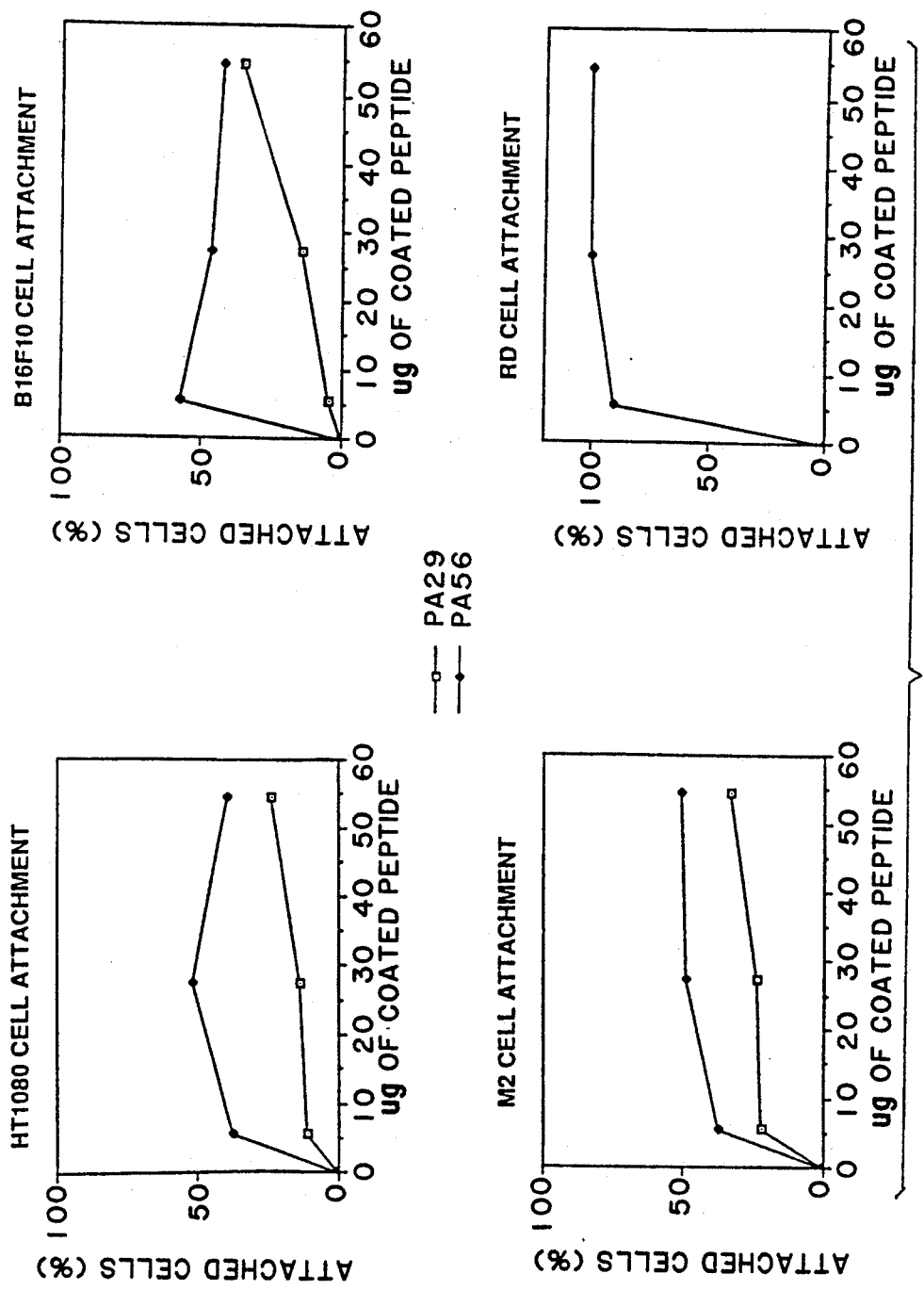
FIG. 22 shows the adhesion to peptides PA56 and PA29.

Another peptide pA56 and its derivative pA29 are also active in cell attachment (see FIG. 22). The location and sequence of these peptides are shown in FIG. 14 and Table III.

EXAMPLE 10

Active peptide pA31-1 and its derivative

Figure 23:
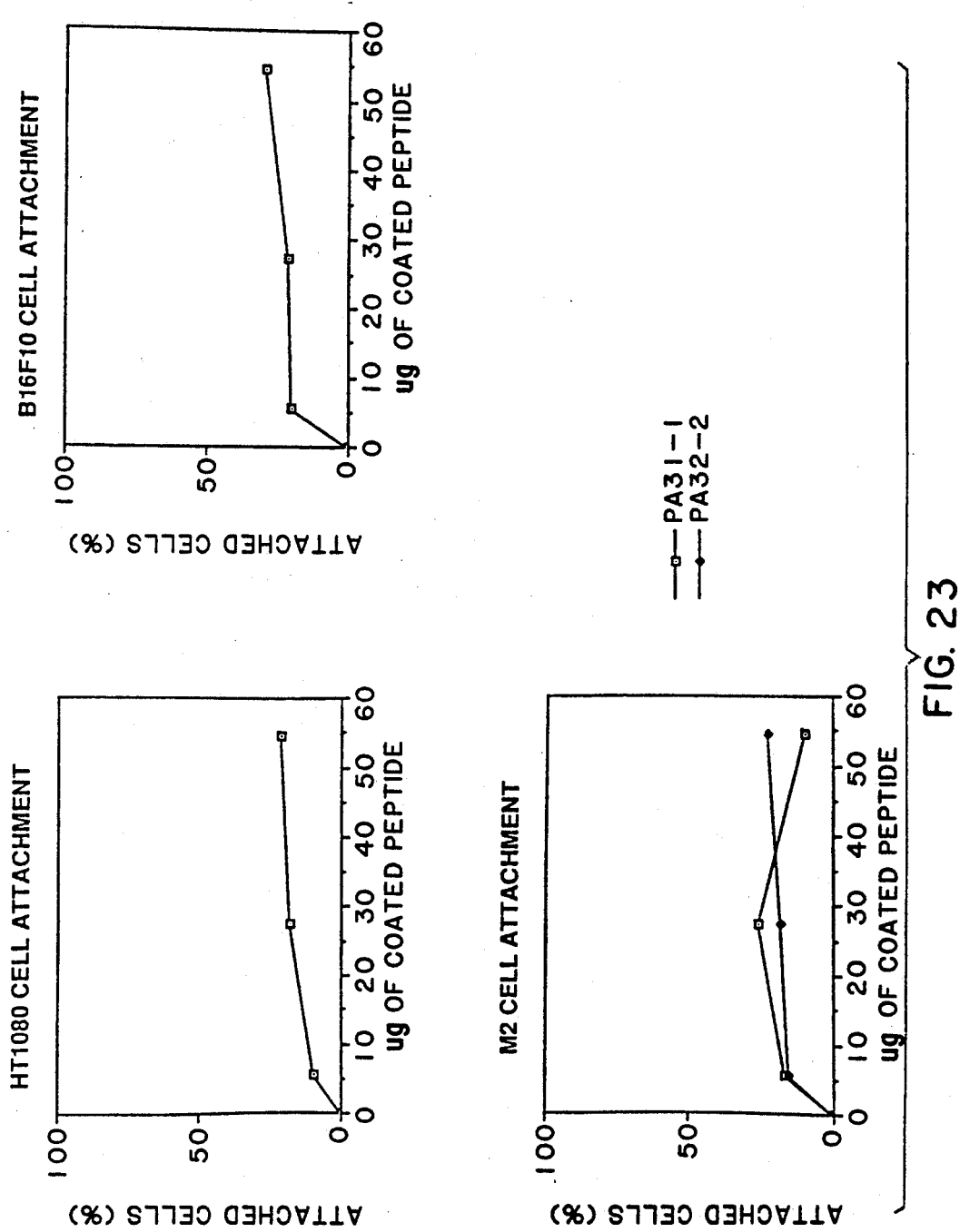
FIG. 23 shows the adhesion to peptides PA31-1 and PA31-2.

The location and sequence of pA31-1 and its derivative pA31-2 are shown in FIG. 14 and Table III. pA31-1 is active for cell attachment (see FIG. 23). pA31-2 contains the amino terminal half of pA31-1 and also has some cell attachment activity.

EXAMPLE 11

Figure 24:
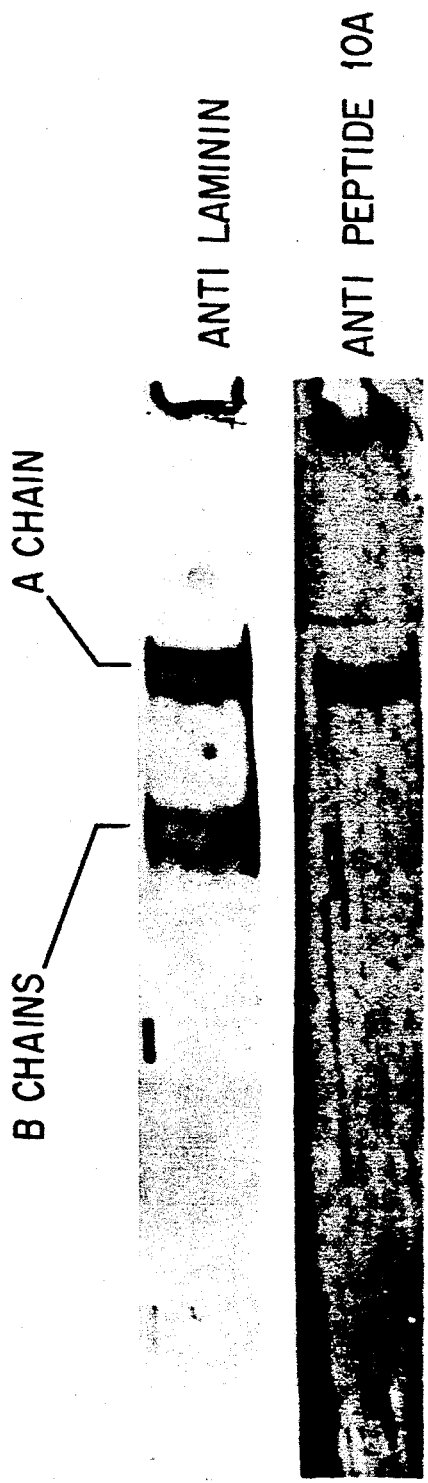
FIG. 24 shows the Western blot of laminin using antibody raised against a synthetic peptide (10A) from the carboxyl end of the A chain.

Inhibition of laminin-mediated neurite outgrowth by antibody to a synthetic peptide p10A The location and sequence of peptide p10A is shown in Table III. This peptide was used to immunize a rabbit. FIG. 24 shows that antibody to p10A specifically reacts in Western blot analysis with the A chain. The antibody blocks laminin-mediated neurite outgrowth by PC-12 cells (see FIG. 25) and by NG 108-15 neuroblastoma cells. Since the corresponding peptide is not active in promoting neurite outgrowth, it can be assumed that the antibody works via stearic hindrance and that the active site is located near the residues contained within the peptide. Accordingly, FIG. 25 shows the effect of antibody to synthetic peptide 10A from the A chain of laminin on inhibiting laminin-mediated neurite outgrowth. The 24 well Falcon dishes were coated with 1.0 ug of laminin for 1 hour in DMEM containing 0.02% BSA. Then, the antibody at various dilutions (e.g 1:3 to 1:10) was added for 1 hour. Unbound antibody was removed by washing and the ability of PC12 cells to extend processes was assessed as previously described.

The invention is also directed to each of the following embodiments:

i) A method for isolating a laminin cell surface receptor from detergent extracts of cells or of cell membranes bound to a laminin affinity column, comprising adding to said cells or cell membranes a protein selected from the group consisting of a peptide of Table III and the expressed protein of a vector containing a DNA sequence of cDNA coding for the A chain of laminin or a segment of DNA coding for a portion of the A chain, wherein the DNA sequence is in association with an expression regulatory sequence.

ii) A peptide of Table III or the expressed protein of a vector containing a DNA sequence of cDNA coding for the A chain of laminin or a segment of DNA coding for a portion of the A chain, wherein the DNA sequence is in association with an expression regulatory sequence and the peptide or protein is attached to the surface of a synthetic fiber.

iii) A peptide of Table III or the expressed protein of a vector containing a DNA sequence of cDNA coding for the A chain of laminin or a segment of DNA coding for a portion of the A chain, wherein the DNA sequence is in association with an expression regulatory sequence and the peptide or protein is attached to the surface of a percutaneous device.

iv) A peptide of Table III or the expressed protein of a vector containing a DNA sequence of cDNA coding for the A chain of laminin or a segment of DNA coding for a portion of the A chain, wherein the DNA sequence is in association with an expression regulatory sequence and the peptide or protein is attached to the surface of a solid substrate to ensure that cells will attach to said substrate.

v) The surface treated substrate comprising a peptide of Table III or the expressed protein of a vector containing a DNA sequence of cDNA coding for the A chain of laminin or a segment of DNA coding for a portion of the A chain, wherein the DNA sequence is in association with an expression regulatory sequence and the peptide or protein is attached to the surface of a solid substrate to ensure that cells will attach to said substrate, wherein the substrate is selected from the group consisting of nitrocellulose, polyester, polyvinyl, polystyrene or ceramic.

vi) A peptide of Table III or the expressed protein of a vector containing a DNA sequence of cDNA coding for the A chain of laminin or a segment of DNA coding for a portion of the A chain, wherein the DNA sequence is in association with an expression regulatory sequence and the peptide or protein is coupled to collagen or agarose.

vii) A peptide of Table III or the expressed protein of a vector containing a DNA sequence of cDNA coding for the A chain of laminin or a segment of DNA coding for a portion of the A chain, wherein the DNA sequence is in association with an expression regulatory sequence and the peptide or protein is in the form of a lotion, salve, gel, colloid, or powder.

viii) A composition for promoting the attachment of cells to a substrate when immobilized on said substrate comprising a peptide of Table III or the expressed protein of a vector containing a DNA sequence of cDNA coding for the A chain of laminin or a segment of DNA coding for a portion of the A chain, wherein the DNA sequence is in association with an expression regulatory sequence.

ix) A method for inhibiting the formation of capillary-like structures by endothelial cells comprising administering to a patient an effective amount of a peptide of Table III or the expressed protein of a vector containing a DNA sequence of cDNA coding for the A chain of laminin or a segment of DNA coding for a portion of the A chain, wherein the DNA sequence is in association with an expression regulatory sequence.

x) An agent for promoting nerve regeneration in damaged tissue comprising, peptide, polymerized peptide of Table III or an expressed protein of a vector containing a DNA sequence of cDNA coding for the A chain of laminin or a segment of DNA coding for a portion of the A chain, wherein the DNA sequence is in association with an expression regulatory sequence and the peptide or protein is in a nerve guide.

xi) An agent for promoting nerve regeneration in damaged tissue comprising polymerized peptide or peptide of Table III or the expressed protein of a vector containing a DNA sequence of cDNA coding for the A chain of laminin or a segment of DNA coding for a portion of the A chain, wherein the DNA sequence is in association with an expression regulatory sequence and the peptide or protein is in combination with biodegradable or biocompatible materials fabricated into a nerve guide.

xii) A method of promoting cell adhesion, migration, cell differentiation, cell growth, and nerve regeneration, which comprises administering to a patient a therapeutically effective amount of a peptide of Table III and peptide expressed by an expression vector containing a DNA sequence of cDNA coding for the A chain of laminin or a segment of DNA coding for a portion of the A chain, wherein the DNA sequence is in association with an expression regulatory sequence.

The invention being thus described, it will be obvious that the same way be varied in many ways. Such variations are not to be regarded as a departure from the spirit and scope of the present invention, and all such modifications as would be obvious to one skilled in the art are intended to be included within the scope of the following claims.

What is claimed is:

1. Peptides and derivatives thereof having laminin A-like activity selected from the group consisting of:
(i) KCQAGTFALRGDNPQG,
(ii) CSKCQAGTFALR,
(iii) XFALRGDNPQG,
(iv) XSRARKQAASIKVAVSADR,
(v) XRKQAASIKVAVS,
(vi) XIKVAVSADR,
(vii) XSRNLSEIKLLISRARK
(viii) GLWNYIEREGKC,
(ix) KPLKTLEENLSRNLSEI,
(x) DRLKPLKTLEENLSRNLSEI,
(xi) XGQIKKSPAVKVTHFKG,
(xii) XGQIKKSPAVKVT, and
(xiii) CIRAYQPQTSSTNYNTLTIL
wherein the X group is an amino acid which is not present in the A chain but is used in coupling the peptide to other materials.

2. The peptides of claim 1 wherein the peptides and derivatives thereof comprise protein polymers or cycled peptides.

3. A pharmaceutical composition comprising a therapeutically effective amount of a peptide of claim 1 and a pharmaceutically acceptable carrier therefor.

4. A pharmaceutical composition comprising 50 ng to 5 ug peptide per $cm^2$ of polymer surface of the polymer of claim 2.

5. A substrate active in promoting epithelial, endothelial or neural cell adhesion, migration, growth, collagenase IV production, neurite outgrowth, tumor formation and heparin binding, comprising the peptides of claim 1 and the expressed material from vectors containing a DNA sequence of cDNA coding for the A chain of laminin or a segment of DNA coding for a portion of the A chain, wherein the DNA sequence is in association with an expression regulatory sequence.

6. A method of stimulating cancer, which comprises administering to an animal a therapeutically effective amount of a peptide of claim 1.

7. The method of claim 6, wherein the animal is a mammal.

8. The method of claim 6, which comprises administering to the animal 0.01 gm to 0.1 gm/gm body weight of the peptide.

9. The method of claim 6, wherein the mode of administration is intravenous, intraperitoneally or via slow release pellet or pump.

10. A prosthetic device having a biologically active surface which exhibits cell attachment activity and growth activity, said surface having linked thereto a peptide of claim 1 or the expressed protein of a vector containing a DNA sequence of cDNA coding for the A chain of laminin or a segment of DNA coding for a portion of the A chain.

11. The prosthetic device of claim 10, wherein said surface comprises a portion of a vascular graft.

12. The prosthetic device of claim 10, wherein said surface comprises synthetic resin fiber.

13. The prosthetic device of claim 10, wherein said surface comprises a portion of a percutaneous device.

14. A method for promoting increased adhesion of epithelial or endothelial cells to vascular prostheses and other artificial organs comprising coating of the prostheses or organ with a protein selected from the group consisting of a peptide of claim 1 or expressed proteins of a vector containing a DNA sequence of cDNA coding for the A chain of laminin or a segment of DNA coding for a portion of the A chain.

15. An anti-adhesion factor for laminin-responsive cells comprising an antibody effective against a peptide of claim 1 or effective against an expressed protein of a vector containing a DNA sequence of cDNA coding for the A chain of laminin or a segment of DNA coding for a portion of the A chain.

16. A method for promoting the migration and growth of epithelial cells and nerves in a wound comprising administering to the wound a therapeutically effective amount of a protein selected from the group consisting of a peptide of claim 1 and the expressed protein of a vector containing a DNA sequence of cDNA coding for the A chain of laminin or a segment of DNA coding for a portion of the A chain.

17. A method for isolating a laminin cell surface receptor from detergent extracts of cells or cell membranes bound to a laminin affinity column, comprising adding to said cells or cell membranes a peptide of claim 1.

* * * * *